(12) United States Patent
Lee

(10) Patent No.: US 12,258,555 B2
(45) Date of Patent: Mar. 25, 2025

(54) AUTOMATED NUCLEIC ACID EXTRACTION DEVICE

(71) Applicant: CATCHGENE CO., LTD., New Taipei (TW)

(72) Inventor: Te-Cheng Lee, New Taipei (TW)

(73) Assignee: CATCHGENE CO., LTD., New Taipei (TW)

( * ) Notice: Subject to any disclaimer, the term of this patent is extended or adjusted under 35 U.S.C. 154(b) by 857 days.

(21) Appl. No.: 17/290,231

(22) PCT Filed: Oct. 8, 2019

(86) PCT No.: PCT/CN2019/109890
§ 371 (c)(1),
(2) Date: Apr. 29, 2021

(87) PCT Pub. No.: WO2020/093824
PCT Pub. Date: May 14, 2020

(65) Prior Publication Data
US 2022/0017890 A1 Jan. 20, 2022

(30) Foreign Application Priority Data
Nov. 9, 2018 (CN) .......................... 201811330464.3

(51) Int. Cl.
*C12N 15/10* (2006.01)
*C12M 1/00* (2006.01)
*C12M 3/00* (2006.01)

(52) U.S. Cl.
CPC ......... *C12N 15/1017* (2013.01); *C12M 23/42* (2013.01); *C12M 29/04* (2013.01); *C12M 47/06* (2013.01); *C12M 47/12* (2013.01)

(58) Field of Classification Search
CPC ... C12N 15/1017; C12M 23/42; C12M 29/04; C12M 47/06; C12M 47/12
(Continued)

(56) References Cited

U.S. PATENT DOCUMENTS

2014/0041758 A1 2/2014 Fournier et al.
2014/0260118 A1 9/2014 Knight
(Continued)

FOREIGN PATENT DOCUMENTS

| CN | 101684463 A | 3/2010 | |
| CN | 106554901 A * | 4/2017 | ........... C12N 15/101 |

(Continued)

OTHER PUBLICATIONS

CN106554901A Machine English Translation (Year: 2017).*

*Primary Examiner* — William H. Beisner
*Assistant Examiner* — Danielle B Henkel
(74) *Attorney, Agent, or Firm* — MUNCY, GEISSLER, OLDS & LOWE, P.C.

(57) ABSTRACT

An automated nucleic acid extraction device includes a base body, a cassette, a driving unit, a moving frame and a syringe. The base body includes a sample accommodating area, a column accommodating area, a cassette accommodating area and a collection tube being arranged in a linear direction. The cassette is arranged in the cassette accommodating area and includes two parallel walls and at least four vertical walls. The parallel walls and the vertical walls jointly form a lysis buffer well, at least one wash buffer well and an elution buffer well. Each vertical wall includes a load-bearing abutment. The driving unit and the moving frame are arranged on the base body. The syringe is arranged on the moving frame and is driven by the driving unit to reciprocate along with the moving frame in the linear direction.

4 Claims, 17 Drawing Sheets

(58) Field of Classification Search
USPC .................................................... 435/306.1
See application file for complete search history.

(56) References Cited

U.S. PATENT DOCUMENTS

| | | |
|---|---|---|
| 2015/0309059 A1 | 10/2015 | Tajima |
| 2016/0033543 A1* | 2/2016 | Stankus ................ B01L 3/502 |
| | | 435/6.12 |
| 2017/0089936 A1 | 3/2017 | Lee |
| 2017/0197213 A1 | 7/2017 | Nielson et al. |

FOREIGN PATENT DOCUMENTS

| | | |
|---|---|---|
| CN | 206204282 U | 5/2017 |
| CN | 206521466 U | 9/2017 |
| TW | 201412981 A | 4/2014 |
| TW | M477925 U | 5/2014 |
| TW | M536238 U | 2/2017 |
| TW | 575454 U | 3/2019 |
| WO | 2008088065 A1 | 7/2008 |
| WO | WO-2011/004653 A1 | 1/2011 |

\* cited by examiner

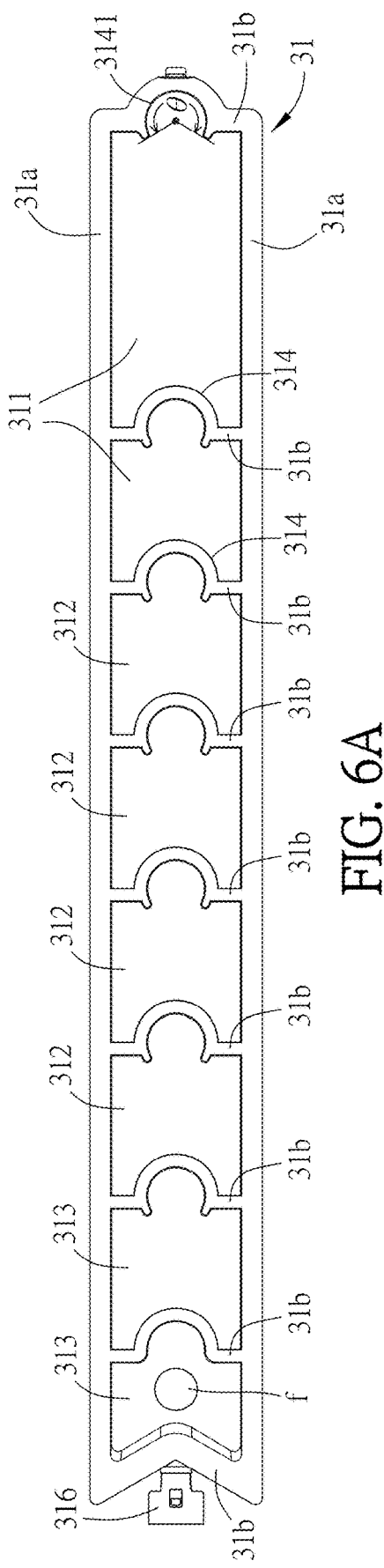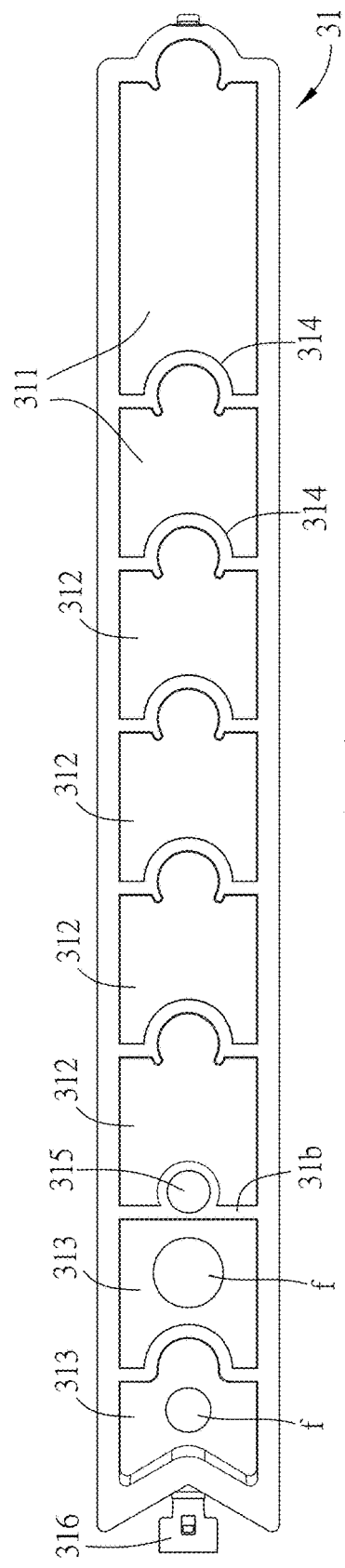
FIG. 6A
FIG. 6B

AUTOMATED NUCLEIC ACID EXTRACTION DEVICE

BACKGROUND

Technology Field

The present disclosure relates to a device and a method, and in particular, to an automated nucleic acid extraction method and device.

Description of Related Art

With the advancement of human genome sequencing technology, the advance in biomedical analysis technology, and the development of big data analysis tools, the era of precision medicine has arrived. The precision medicine is a customized medical model based on human genome information, combined with related internal environmental information such as proteome and metabolome, to design optimal treatment plans for patients to maximize therapeutic effects and minimize side effects.

Blood is a red opaque viscous liquid that flows through the blood vessels and heart of the human body. The main contents of blood include plasma, blood cells, and genetic material (chromosomes and genes). Among them, cfDNA (cell free DNA) are degraded DNA fragments found in plasma that are freely circulating in the blood stream, and ctDNA are circulating tumor DNA, which refers to DNA fragments in cfDNA released from a tumor.

Almost everyone's blood contains free DNA fragments (cfDNA), which may be derived from cell apoptosis or necrosis, or may enter the blood by active release (severe exercise). However, the amount of cfDNA in the blood is very low. In 1 ml of plasma, the amount of cfDNA is between about 1 ng and 100 ng, and the amount of ctDNA is much lower, which is only 0.1%~5% of cfDNA.

Some studies have indicated that the total amount of cfDNA in peripheral blood of patients with tumors is higher than that of healthy people. Based on these studies, if the amount of cfDNA is increased, it can be a good indication as a means for screening tumors. Therefore, the purification of a liquid biopsy to obtain a very small amount of cfDNA (a type of nucleic acid) is the first step in precision medicine.

At present, researchers in the field have devoted themselves to developing devices and methods for extracting nucleic acids such as cfDNA or ctDNA. For example, CN101684463A provides a method for rapidly processing and extracting nucleic acids from various trace clinical samples, which comprises the following steps: (a) adding the clinical sample to the lysis solution and mixing; (b) sucking the clinical sample to flow through a filter membrane, wherein the nucleic acid components in the sample are adsorbed on the filter membrane due to the specific adsorption of the membrane, and the filtrate is a waste liquid containing cell debris and proteins; (c) sucking the wash solution to flow through the filter membrane for washing the residual proteins or other components on the filter membrane, and discarding the filtrate; and (d) sucking the elution liquid to flow through the filter membrane for eluting the nucleic acid components adsorbed on the filter membrane to obtain an aqueous nucleic acid solution without containing other impurities for nucleic acid amplification.

TWM477925U provides a sample extraction device, including a suction member. The suction member includes a first upper part, a middle part disposed below the first upper part and communicating with the first upper part, and a suction part disposed below the lower part and communicating with the middle part, wherein the middle part has an inner diameter smaller than the inner diameter of the first upper part, and the suction part has an inner diameter smaller than the inner diameter of the middle part. Accordingly, the first upper part or the middle part cooperates and abuts against the outer circumference of the column member, and the suction member sucks the specific liquid to the column member. The sample extraction device further comprises: a column member; and a connecting member, thereby extracting expected materials from the sample.

TWM536238U provides a machine for automatic nucleic acid extraction, which includes: a machine bottom plate, on which a tray holder can be moved along a horizontal track; a frame vertically arranged above the machine bottom plate and having a vertical track configured thereon; a vertical movement unit including a substrate, a substrate track configured above the substrate, a moving block arranged along the substrate track, and a syringe fixing unit located below the moving block and fastened to the substrate for a syringe to be erected thereon; and a piston thruster fixing unit for configuring a piston thruster, so that when the moving block moves up and down along the substrate track, the piston thruster can be carried to move so as to enable the syringe to generate positive pressure or negative pressure. In addition, the substrate arranged along the vertical track can drive the moving block and the syringe fixing unit to move up and down corresponding to the corresponding frame.

TW201412981A provides a method and device for extracting nucleic acid, which uses air pressure to extract nucleic acid. The upper end of the purification tube is connected with a device capable of providing a positive or negative air pressure, and the sample, the wash liquid and the elution liquid can be sucked/ejected through the lower tip portion of the purification tube, thereby achieving the effect of easily extracting nucleic acid without the need of a centrifuge.

Although the above-mentioned conventional technologies exist, these conventional technologies still have the disadvantage of fail to extract cfDNA or ctDNA in large quantities. Therefore, if an automated nucleic acid extraction device, which can extract a large amount of cfDNA or ctDNA to increase the yield, can be developed, it will provide a breakthrough in precision medicine.

SUMMARY

An objective of this disclosure is to provide an automated nucleic acid extraction device and an automated nucleic acid extraction method. Compared with the conventional technologies, the automated nucleic acid extraction device and method of this disclosure can rapidly and conveniently extract the nucleic acid (e.g. cfDNA and ctDNA) with higher yield and higher concentration from the specimen.

Accordingly, this disclosure provides an automated nucleic acid extraction device, which comprises a base body, a cassette, a driving unit, a moving frame, and a syringe. The base body comprises a sample accommodating area, a column accommodating area, a cassette accommodating area and a collection tube. The sample accommodating area, the column accommodating area, the cassette accommodating area and the collection tube are arranged in a linear direction. The cassette is arranged in the cassette accommodating area. The cassette includes two parallel walls and at least two vertical walls, and the parallel walls and the vertical walls jointly form a lysis buffer well, at least one wash buffer well and an elution buffer well. Each of the vertical walls forming the lysis buffer well, the wash buffer wells and the elution buffer well includes a load-bearing abutment. The lysis buffer well, the wash buffer well and the elution buffer well are arranged in the linear direction, and the load-bearing abutment is provided with an arcuate wall or a polygonal wall. The driving unit is arranged on the base body. The moving frame is arranged on the base body vertically and driven by the driving unit to reciprocate in the linear direction. The syringe is arranged on the moving frame and is moved along with the moving frame.

In one embodiment, the sample accommodating area comprises a sample accommodating space and a binding buffer accommodating space.

In one embodiment, the column accommodating area further comprises a sample tip accommodating space and a column tip accommodating space.

In one embodiment, the automated nucleic acid extraction device further comprises a sample tip, which is movably disposed in the sample tip accommodating space.

In one embodiment, the automated nucleic acid extraction device further comprises a column tip, which is movably disposed in the column tip accommodating space.

In one embodiment, the syringe is detachably connected to the sample tip or the column tip.

In one embodiment, the sample accommodating space is used for accommodating a biological sample and a lysis buffer for performing a lysis reaction, the binding buffer accommodating space is used for accommodating a binding buffer and the lysate for performing a binding reaction, and the lysis buffer well is used for accommodating a lysis buffer, a defoaming agent and reaction residues, the wash buffer wells are used for accommodating a wash buffer, the elution buffer wells are used for accommodating an elution buffer, the sample tip accommodating space is used for accommodating the sample tip, and the column tip accommodating space is used for accommodating the column tip.

In one embodiment, an arc angle of the arcuate wall is greater than or equal to 90 degrees.

In one embodiment, the vertical wall between the wash buffer well and the elution buffer well has a complete hollow cylindrical structure so as to form a filter accommodating space for accommodating a filter.

In one embodiment, the polygonal wall comprises at least two supporting walls, and an included angle between the supporting walls is less than 180 degrees.

In one embodiment, a bottom portion of the elution buffer well is provided with a recess portion.

In one embodiment, the cassette further comprises an elastic fastener for detachably fastening the cassette to the cassette accommodating area.

This disclosure further provides an automated nucleic acid extraction method applied to the above-mentioned automated nucleic acid extraction device. The automated nucleic acid extraction method comprises the following steps of: using the syringe in cooperate with a column tip to suck a mixed reactant in the binding buffer accommodating space, so that nucleic acids contained in the reactant are bound to a membrane inside the column tip, and to eject a reaction residue to the cassette, so that nucleic acids inside the reaction residue are bound to the membrane; using the syringe in cooperate with the column tip to suck the wash buffer in the at least one wash buffer well through the membrane, and then using the syringe in cooperate with the column tip to eject the wash buffer through the membrane; and using the syringe in cooperate with the column tip to suck the elution buffer in the elution buffer well through the membrane, and then using the syringe in cooperate with the column tip to eject through the membrane the elution buffer containing the nucleic acids to the collection tube.

In one embodiment, in the automated nucleic acid extraction method, in the step of ejecting the reaction residue to the cassette and the step of using the syringe in cooperate with the column tip to eject the wash buffer through the membrane, the abutting portion of the column tip is abutted against the load-bearing abutment of the cassette before ejecting the reaction residue or the wash buffer.

In one embodiment, after the step of abutting the abutting portion of the column tip against a load-bearing abutment of the cassette and then ejecting the reaction residue or the wash buffer, the automated nucleic acid extraction method further comprises a step of: abutting the abutting portion of the column tip against the load-bearing abutment of the cassette and moving the syringe in a direction perpendicular to the linear direction up and down for a distance less than or equal to 5 mm.

As mentioned above, the lysis buffer well, the wash buffer well and the elution buffer well formed by the parallel walls and the vertical walls can contain a large volume of solution; and the wash buffer wells and the elution buffer well are respectively configured with a load-bearing abutment, which can prevent the sample tip or the column tip from falling off the syringe and being separated from the syringe after the syringe has ejected a large volume of solution. In addition, since the cassette and the accommodating space are arranged in a linear direction and the moving frame and the syringe can reciprocate in the linear direction, the effect of automated nucleic acid extraction in a linear direction can be achieved, thereby avoiding sample contamination and improving extraction efficiency. The automated nucleic acid extraction device of the present disclosure can indeed rapidly and conveniently extract nucleic acids (e.g. cfDNA and ctDNA) with a higher yield and a higher concentration from the specimen. Furthermore, compared with the conventional art, which adopts the linear movement of the cassette and the accommodating space (i.e., the cassette moves relative to the desktop, but the syringe does not move), the present disclosure adopts the linear movement of the moving frame and the syringe (i.e., the syringe moves relative to the desktop, but the cassette does not move). Therefore, the automated nucleic acid extraction device of the present disclosure can have a smaller operating space, which is about the length of the cassette and the accommodating space, wherein the operating space for linear movement of the cassette and the accommodating space in the prior art is about 2 to 3 times the length of the cassette and the accommodating space. As a result, the volume of the automated nucleic acid extraction device of the present disclosure is smaller, and the operation space of the user can be saved.

BRIEF DESCRIPTION OF THE DRAWINGS

FIG. 6A is a top view of a cassette of the automated nucleic acid extraction device according to an embodiment of this disclosure.

FIG. 6B is a top view of a cassette of the automated nucleic acid extraction device according to another embodiment of this disclosure.

DETAILED DESCRIPTION OF THE DISCLOSURE

The automated nucleic acid extraction device of this invention will be apparent from the following embodiments with reference to the accompanying drawings, wherein the same references relate to the same elements.

The automated nucleic acid extraction device of the present disclosure can rapidly and conveniently extract nucleic acids (e.g. cfDNA and ctDNA) with a higher yield and a higher concentration from the specimen. In particular, the specimen may be, for example but not limited to, blood, plasma, urine, saliva, tissue fluid or tissue. The structure and features of the automated nucleic acid extraction device will be described in the following embodiments.

Figure 1:
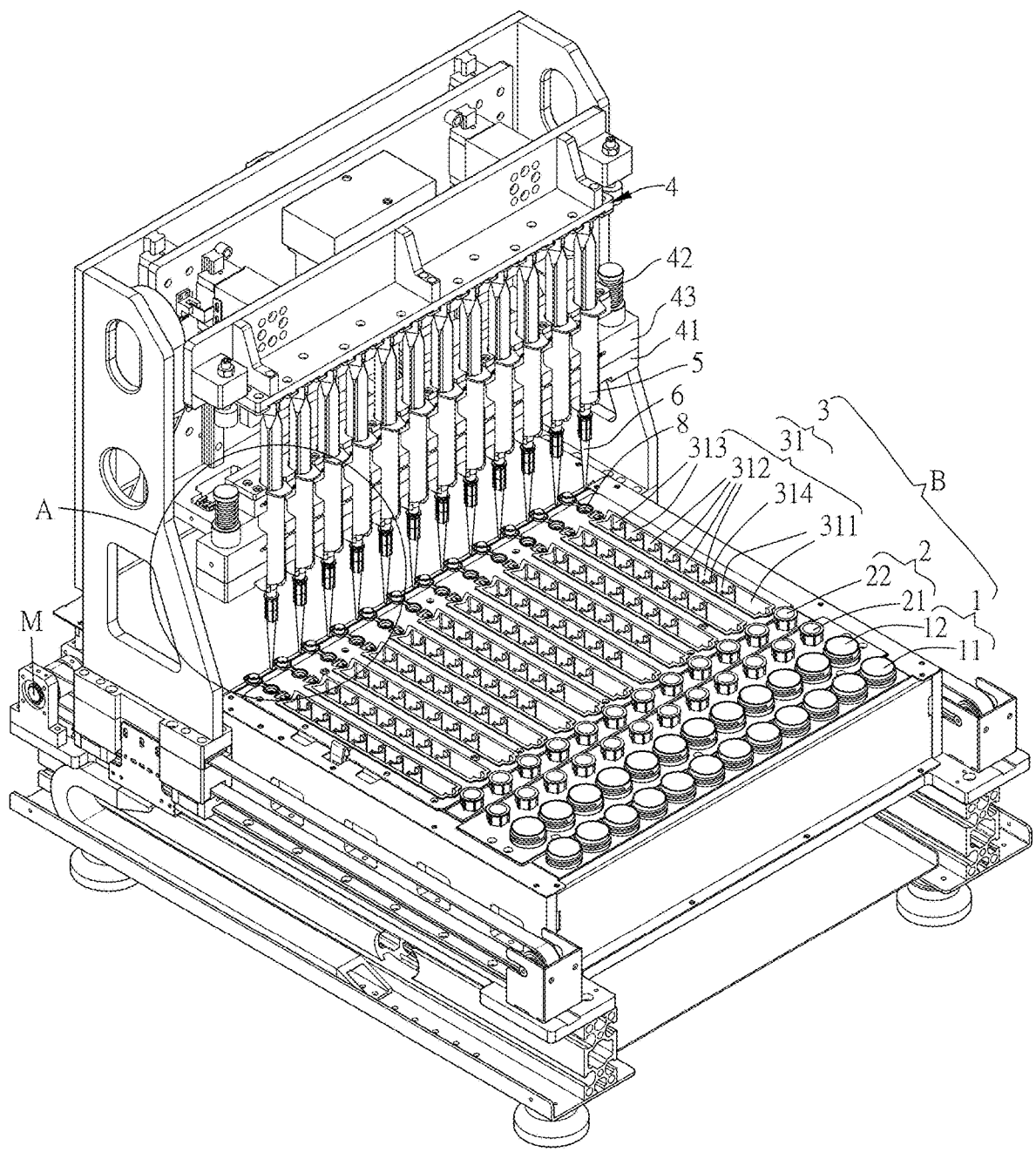
FIG. 1 is a schematic diagram showing an automated nucleic acid extraction device according to an embodiment of this disclosure.
Figure 2:
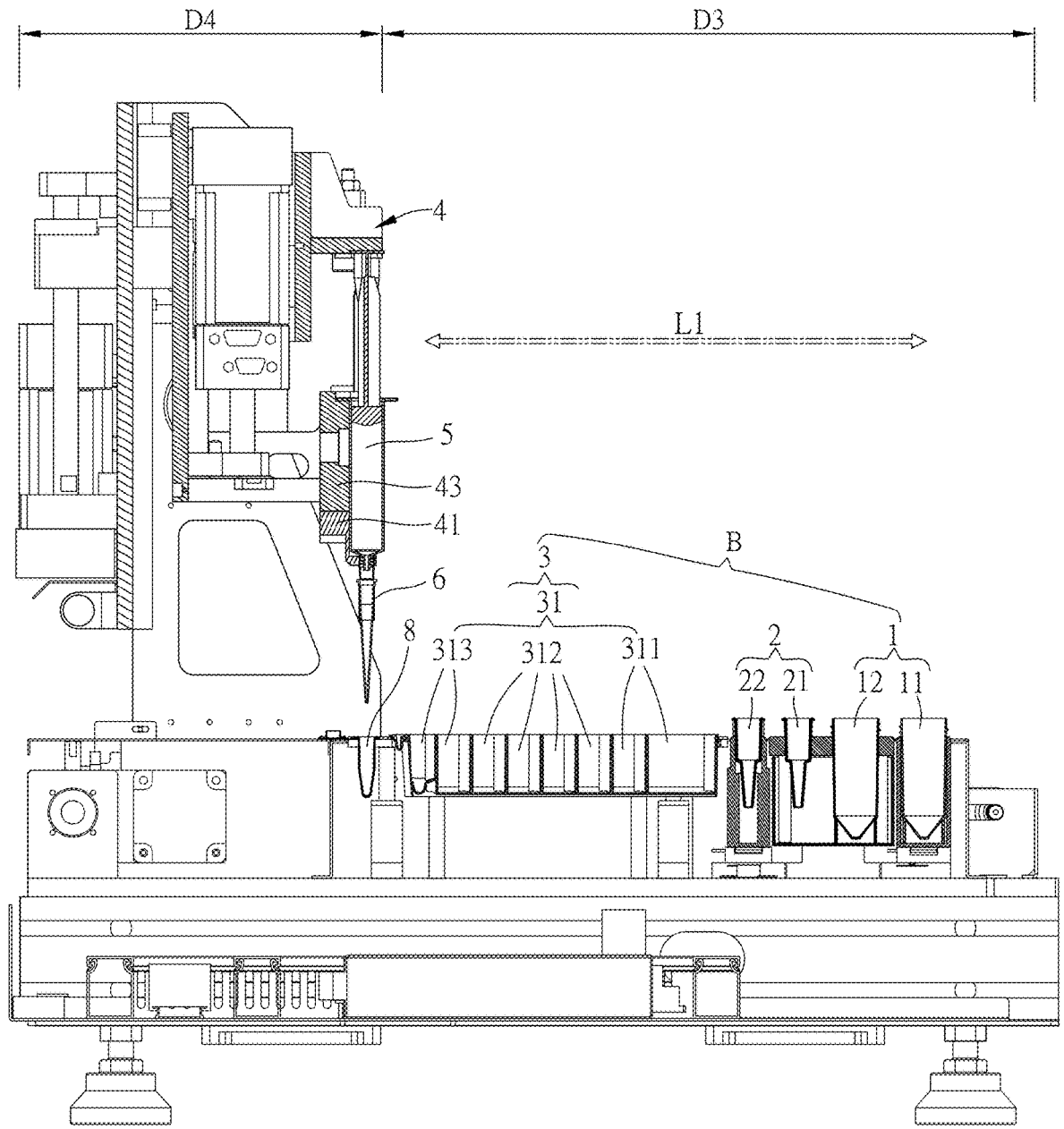
FIG. 2 is a side view of the automated nucleic acid extraction device according to an embodiment of this disclosure.

Please refer to FIG. 1 and FIG. 2, wherein FIG. 1 is a schematic diagram showing an automated nucleic acid extraction device according to an embodiment of this disclosure, and FIG. 2 is a side view of the automated nucleic acid extraction device according to an embodiment of this disclosure.

As shown in FIGS. 1 and 2, the automated nucleic acid extraction device comprises a base body B, a cassette 31, a driving unit M, a moving frame 4, and a syringe 5.

The base body B comprises a sample accommodating area 1, a column accommodating area 2, and a cassette accommodating area 3. The sample accommodating area 1 comprises a sample accommodating space 11 and a binding buffer accommodating space 12. The sample accommodating area 1, the column accommodating area 2 and the cassette accommodating area 3 are arranged in a linear direction L1. In particular, the sample accommodating area 1, the column accommodating area 2 and the cassette accommodating area 3 can be arranged in the linear direction L1, for example but not limited to, in the order of (from right to left on the drawing): the sample accommodating area 1, the column accommodating area 2 and the cassette accommodating area 3; the column accommodating area 2, the cassette accommodating area 3 and the sample accommodating area 1; the cassette accommodating area 3, the sample accommodating area 1 and the column accommodating area 2; or the cassette accommodating area 3, the column accommodating area 2 and the sample accommodating area 1.

Referring to FIG. 2 in view of FIG. 6A, the cassette 31 is arranged in the cassette accommodating area 3. The cassette 31 includes two parallel walls 31a and at least two vertical walls 31b, and the parallel walls 31a and the vertical walls 31b jointly form a lysis buffer well 311, at least one wash buffer well 312 and an elution buffer well 313. Each of the vertical walls 31b forming the lysis buffer well 311, the wash buffer wells 312 and the elution buffer well 313 includes a load-bearing abutment 314. The lysis buffer well 311, the wash buffer well 312 and the elution buffer well 313 are arranged in the linear direction L1. In this embodiment, the cassette 31 includes nine vertical walls 31b, and the parallel walls 31a and the vertical walls 31b jointly form two lysis buffer wells 311, four wash buffer wells 312, and two elution buffer wells 313. To be noted, the numbers of the lysis buffer well 311, the wash buffer wells 312 and the elution buffer well 313 can be adjusted based on the requirement of the user. For example, if the sample is a tissue that is difficult to be extracted, the numbers of the lysis buffer wells 311 and the elution buffer wells 313 can be increased, and this disclosure is not limited. In addition, the lysis buffer wells 311, the wash buffer well 312 and the elution buffer well 313 formed by the parallel walls 31a and the vertical walls 31b of the cassette 31 can accommodate a large volume of buffers (e.g. the lysis buffer, the wash buffer and/or the elution buffer), such as, for example but not limited to, 2 ml or more, 5 ml or more, or 10 ml or more.

Referring to FIGS. 1 and 2, in this embodiment, the driving unit M is arranged on the base body B, and the moving frame 4 is arranged on the base body B vertically and driven by the driving unit M to reciprocate in the linear direction L1. The syringe 5 is arranged on the moving frame 4 and is moved along with the moving frame 4. In particular, although the driving unit M shown in the drawings is a transmission belt, the driving unit M can also be any of other driving devices such as a linear motion module or any device for driving the moving frame 4 to move linearly. This disclosure is not limited.

Figure 4:
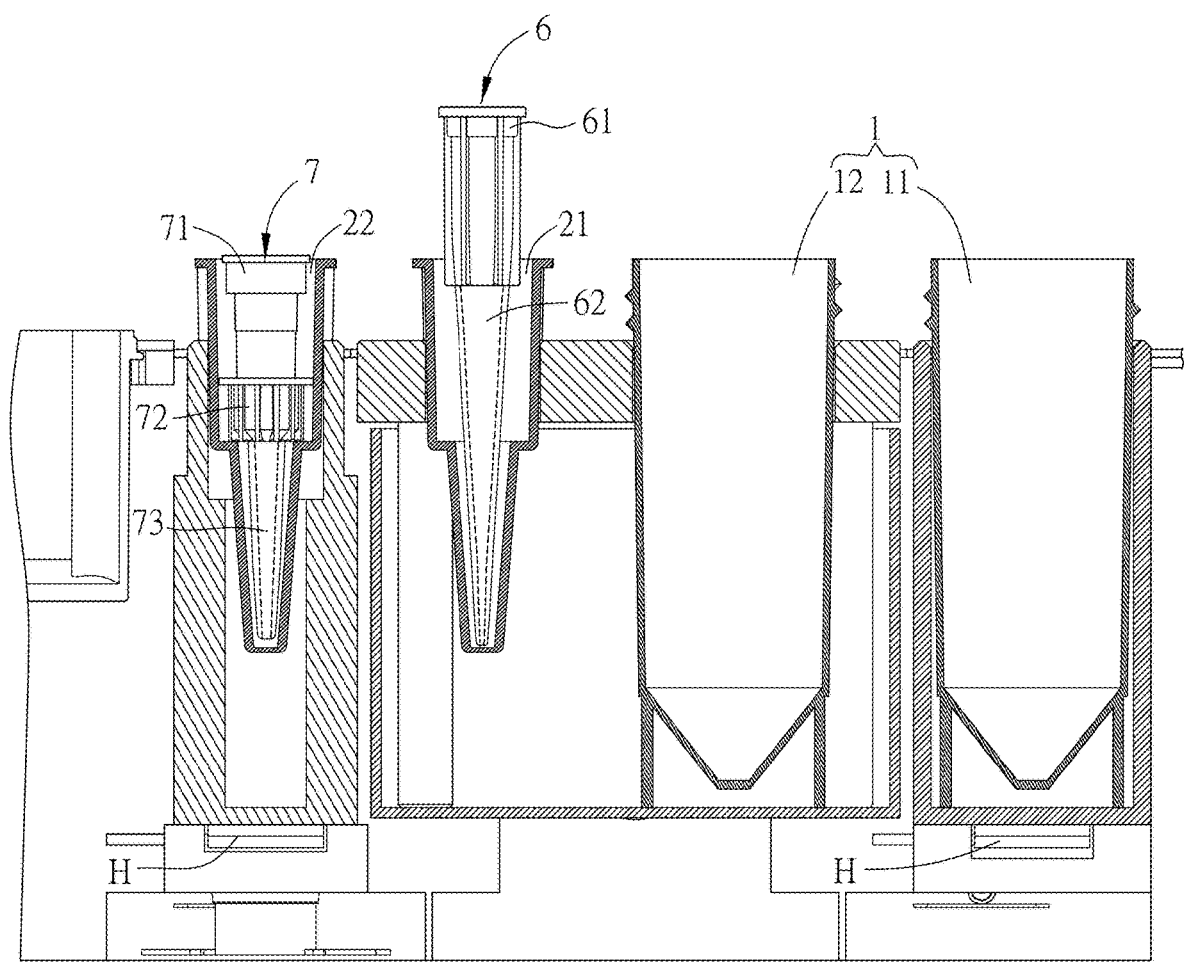
FIG. 4 is a partial view of the automated nucleic acid extraction device according to an embodiment of this disclosure.

Referring to FIGS. 1, 2 and 4, in this embodiment, the column accommodating area 2 further comprises a sample tip accommodating space 21 and a column tip accommodating space 22.

As shown in FIG. 4, in this embodiment, the automated nucleic acid extraction device further comprises a sample tip 6, which is movably disposed in the sample tip accommodating space 21. In this embodiment, the automated nucleic acid extraction device further comprises a column tip 7, which is movably disposed in the column tip accommodating space 22. In particular, the syringe 5 is detachably connected to the sample tip 6 or the column tip 7.

Referring to FIGS. 1 to 3A, the automated nucleic acid extraction device further comprises a collection tube 8, and the collection tube 8, the cassette 31 and these accommodating areas are arranged in the linear direction L1. Preferably, the collection tube 8 can be disposed adjacent to the cassette 31 (however, this disclosure is not limited thereto). Since the automated nucleic acid extraction method is to perform the extraction along the linear direction L1, and then eject the eluate into the collection tube 8 in the last step, the collection tube 8 is disposed adjacent to the cassette 31 and arranged along the linear direction L1, which is in the same direction as the moving direction of the moving frame 4. This configuration can prevent the moving frame 4 from repeatedly passing through the position above the collection tube 8 during the process of automated nucleic acid extraction, which may cause the cross contamination.

In this embodiment, the sample accommodating space 11 is used for accommodating a biological sample and a lysis buffer for performing a lysis reaction. In this embodiment, the biological sample comprises, for example but not limited to, blood, plasma, urine, saliva, tissue fluid or tissue. The binding buffer accommodating space 12 is used for accommodating a binding buffer and the lysate for performing a binding reaction. The lysis buffer well 311 is used for accommodating a lysis buffer, a defoaming agent and reaction residues. The wash buffer wells 312 are used for accommodating a wash buffer. The elution buffer wells 313 are used for accommodating an elution buffer. The sample tip accommodating space 21 is used for accommodating the sample tip 6. The column tip accommodating space 22 is used for accommodating the column tip 7. In this embodiment, the sample accommodating space 11, the binding buffer accommodating space 12, the lysis buffer well 311, and the wash buffer wells 312 can accommodate the specimen or buffers of, for example but not limited to, 30 mL. Compared with the conventional technology, which generally accommodates 2 mL, this embodiment can provide a larger volume for accommodating specimen. The increased volume of the lysis buffer can improve the lysis reaction so as to increase the concentration of nucleic acids, and the increased volume of the wash buffer can clean the residues remained in the column tip 7, thereby increasing the concentration and purity of the nucleic acids obtained in the following extraction steps. In this embodiment, the numbers of the lysis buffer well, the wash buffer wells, and the elution buffer wells can be adjusted based on the actual needs of the user, and this disclosure is not limited.

Figure 3A:
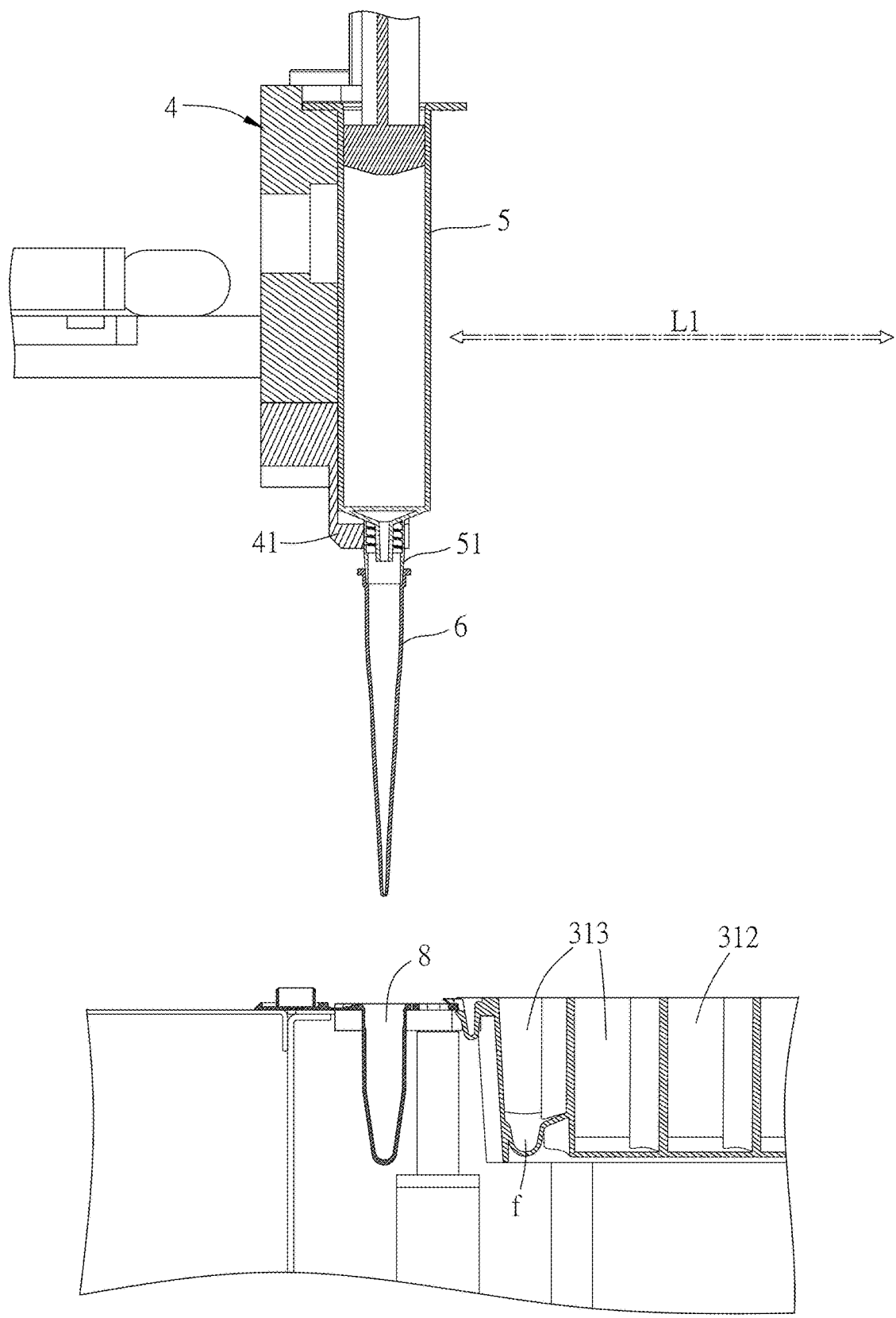
FIG. 3A is a partial view of the automated nucleic acid extraction device according to an embodiment of this disclosure.
Figure 3B:
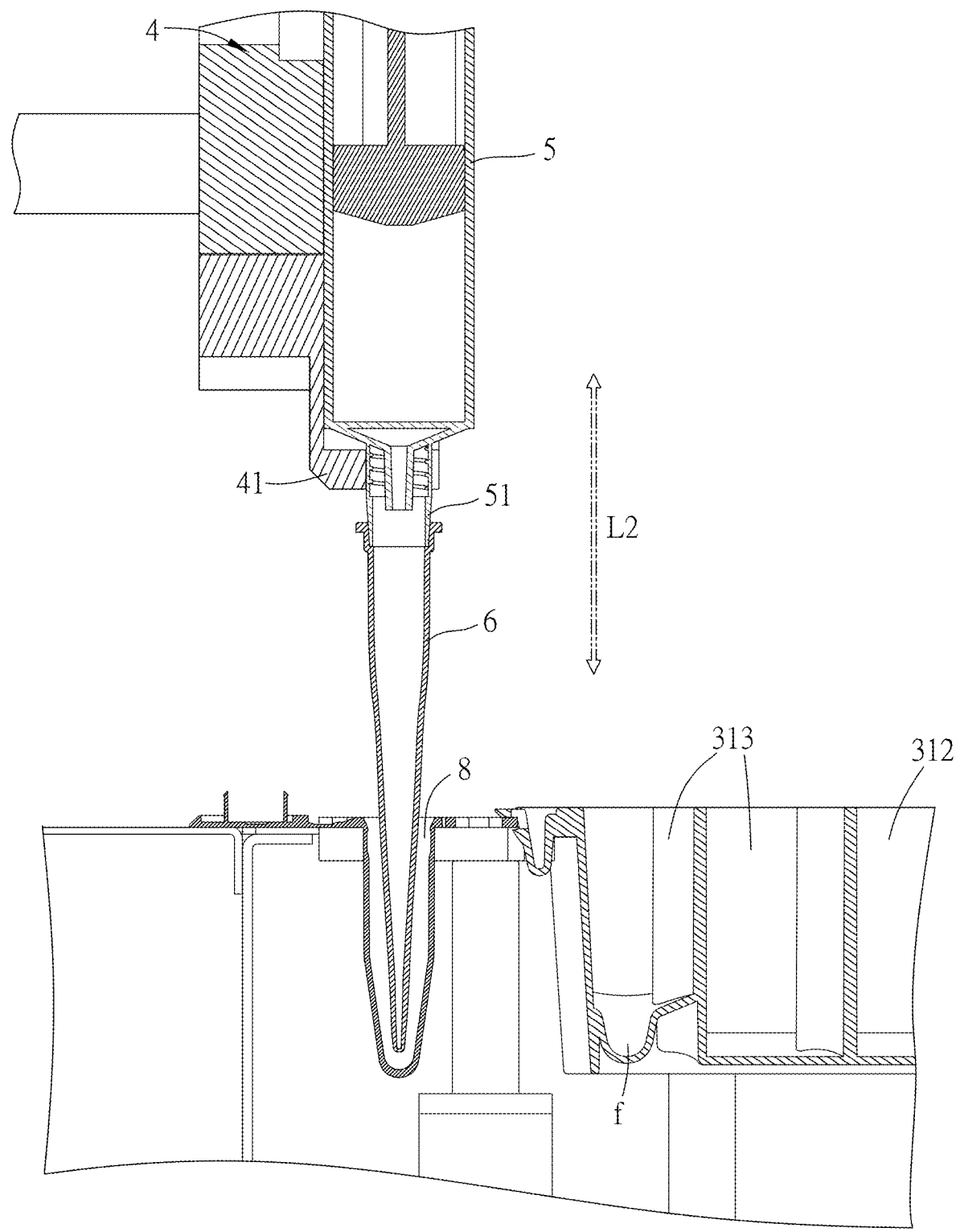
FIG. 3B is a partial view of the automated nucleic acid extraction device according to an embodiment of this disclosure.
Figure 3C:
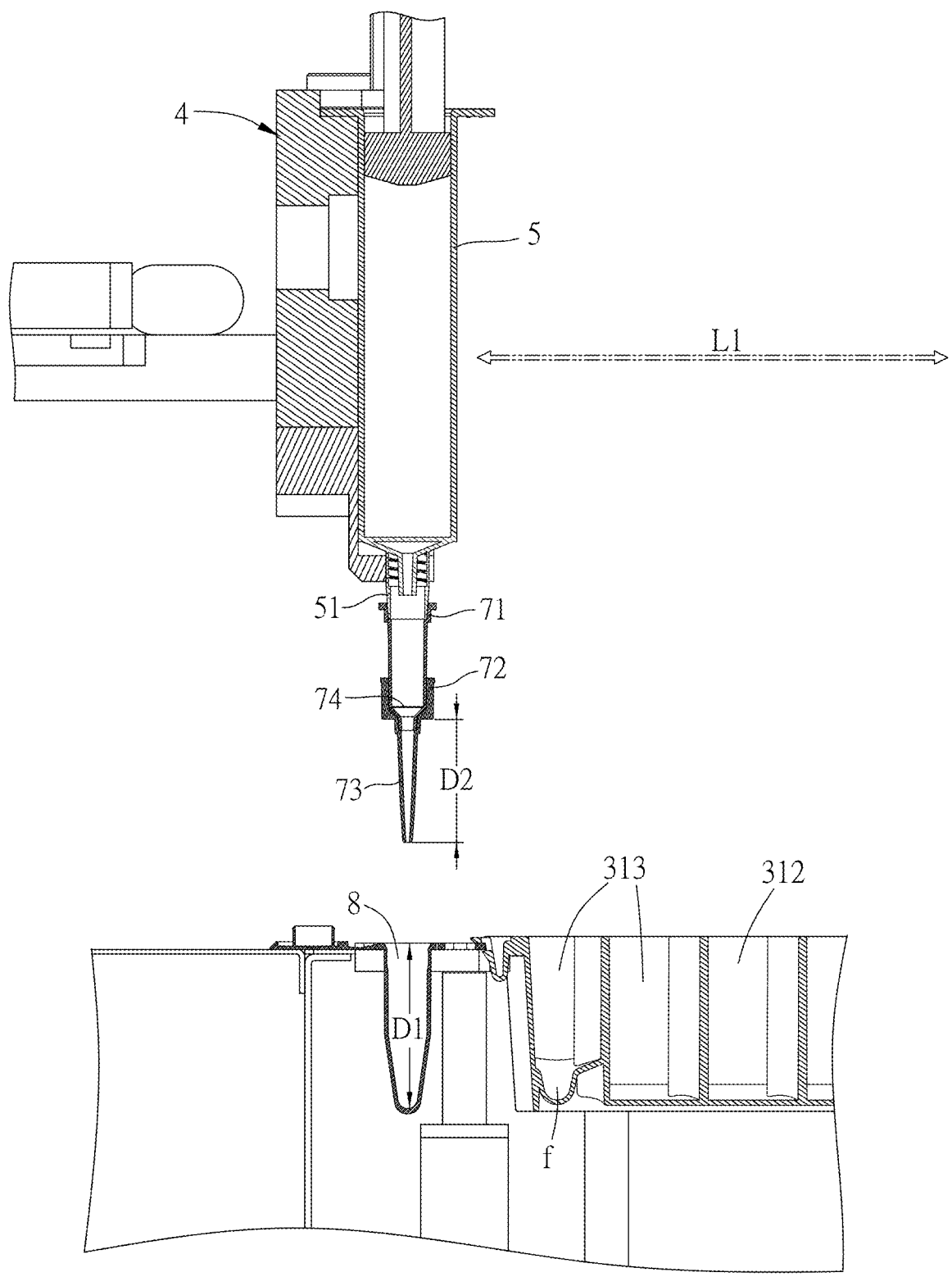
FIG. 3C is a partial view of the automated nucleic acid extraction device according to an embodiment of this disclosure.

Referring to FIG. 3C, a membrane 74 is configured inside the column tip 7. The material of the membrane 74 can be, for example but not limited to, a silica membrane, which carries positive charges. In the process of nucleic acid extraction, the nucleic acid contained in the specimen can carry negative charges, so that the nucleic acids can be attached to the membrane 74 by the attraction characteristics of positive and negative charges. Afterwards, the nucleic acids attached to the membrane 74 will be extracted in the subsequent procedures.

In this embodiment, the base body B further comprises at least one heater H, which is disposed below the sample accommodating space 11 and/or the column tip accommodating space 22. Herein, when the heater H is provided below the sample accommodating space 11, it can promote the lysis reaction between the biological sample and the lysis buffer, so that the lysis of biological sample can be more complete, thereby increasing the concentration of nucleic acids obtained by the following extraction procedure. When the heater H is provided below the column tip accommodating space 22, it can promote the volatilization of the residual solvent on the membrane 74 of the column tip 7, thereby increasing the concentration and purity of nucleic acids obtained by the following extraction procedure. In particular, when the nucleic acid to be extracted is ribonucleic acid (RNA), the heater H below the sample accommodating space 11 may be turned off (that is, it is not heated during the lysis reaction) to prevent the decomposition of RNA, which may affect the concentration of RNA after extraction.

Referring to FIGS. 3A and 3B, the bottom portion of the elution buffer well 313 is provided with a recess portion f. Based on this design, the elution process of the specimen can be finished with a smaller amount of elution buffer, thereby increasing the concentration of the extracted nucleic acids. In particular, although the drawings show that only the elution buffer well 313 adjacent to the collection tube 8 is configured with a recess portion f, it is possible to configure a recess portion f in any of other elution buffer wells 313. This disclosure is not limited. In addition, the volume of the elution buffer can be, for example but not limited to, 1 mL, 500 µL, 200 µL, 100 µL, 50 µL, 30 µL, etc., and it can be adjusted according to the needs of the user. This disclosure is not limited.

Figure 6C:
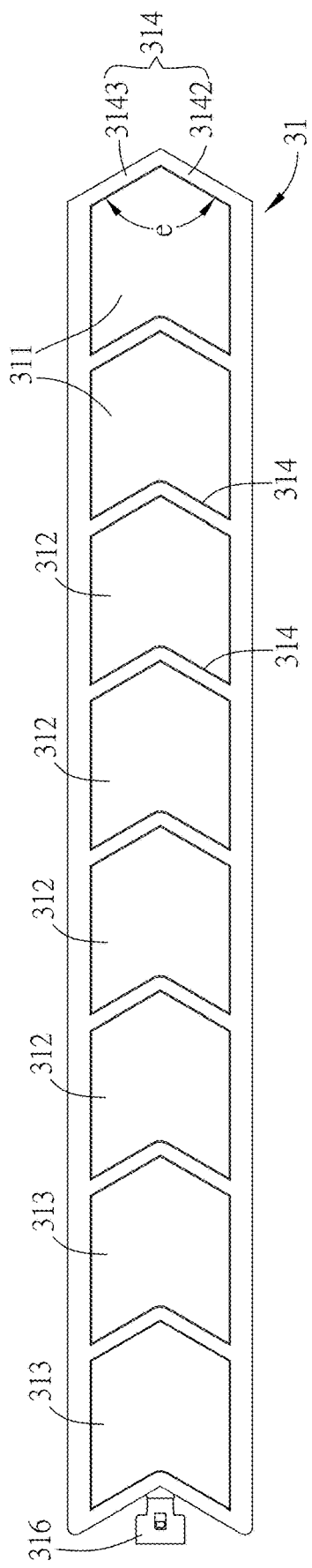
FIG. 6C is a top view of a cassette of the automated nucleic acid extraction device according to another embodiment of this disclosure.
Figure 8A:
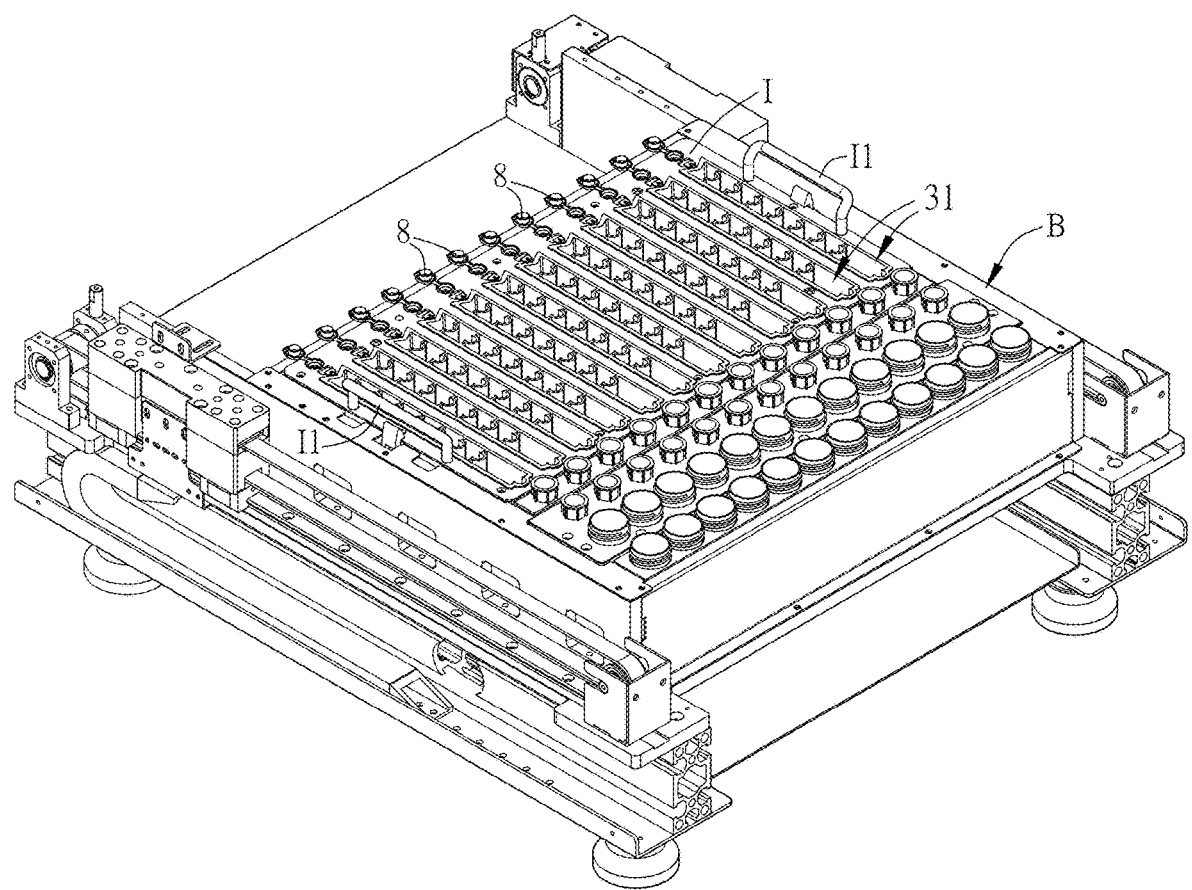
FIG. 8A is a partial enlarged view of the automated nucleic acid extraction device of FIG. 1.
Figure 8B:
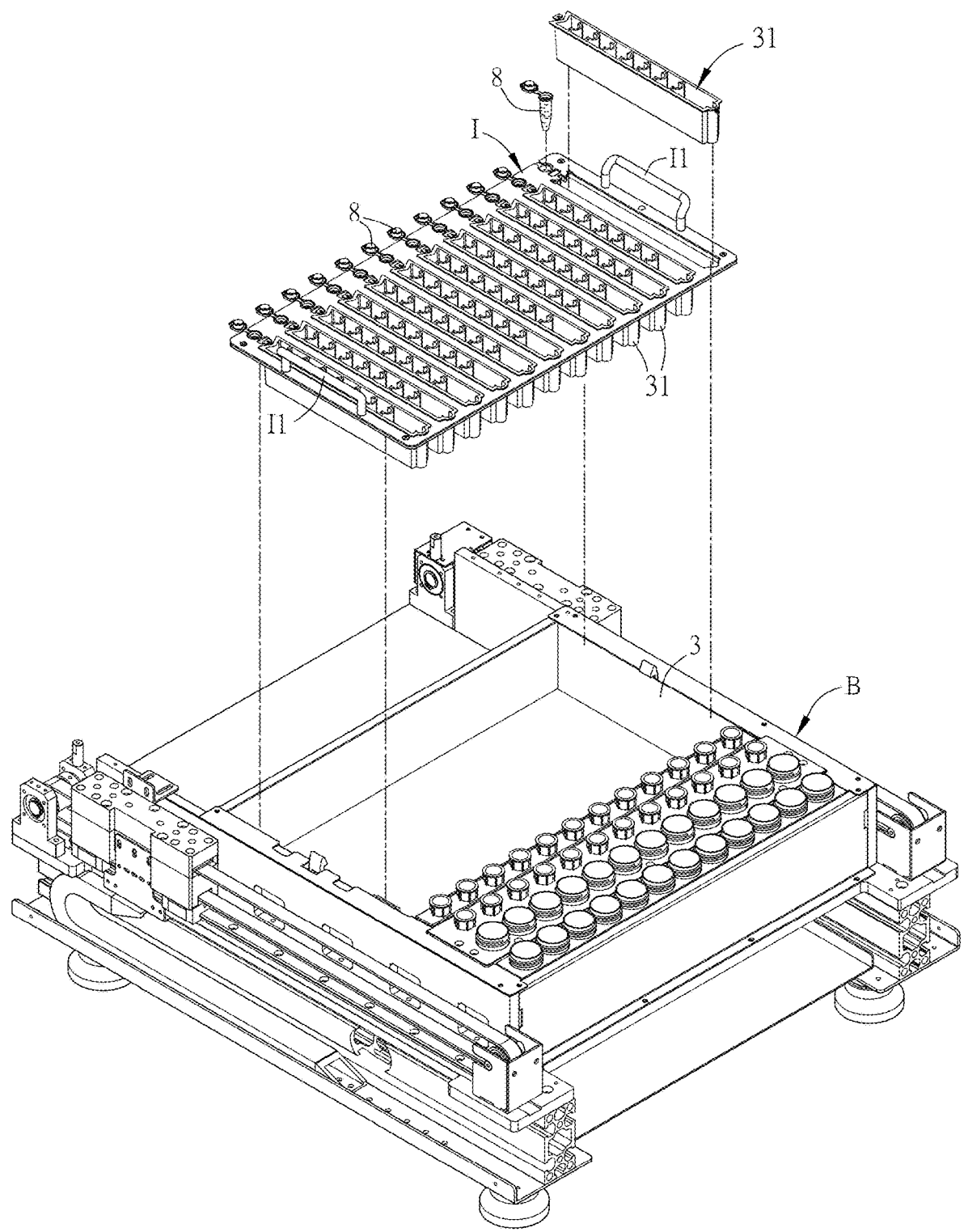
FIG. 8B is an exploded view of the automated nucleic acid extraction device of FIG. 8A.

Referring to FIGS. 6A to 6C, the cassette 31 further comprises an elastic fastener 316 for detachably fastening the cassette 31 to the cassette accommodating area 3. In particular, the details of the structure will be illustrated with reference to FIGS. 8A and 8B, wherein FIG. 8A is a partial enlarged view of the automated nucleic acid extraction device of FIG. 1, and FIG. 8B is an exploded view of the automated nucleic acid extraction device of FIG. 8A. The automated nucleic acid extraction device of this embodiment further comprises an iron frame I, which is detachably disposed on the base body B. In practice, the user may place a plurality of cassettes 31 and collection tubes 8 on the iron frame I, and then put the iron frame I as well as the cassettes 31 and collection tubes 8 on the base body B, so that the user can easily arrange multiple cassettes 31 and collection tubes 8. Alternatively, the user may arrange the iron frame I on the base body B, and then dispose the cassettes 31 and collection tubes 8 on the iron frame I, and this disclosure is not limited. Moreover, after utilizing the automated nucleic acid extraction device to extract the nucleic acids, the user may move the iron frame I as well as the multiple cassettes 31 and collection tubes 8 out of the base body B. In particular, the iron frame I may be configured with two handles I1, so that the user can easily move the iron frame I into or out of the base body B accordingly.

Referring to FIG. 4, the sample tip 6 comprises an installing portion 61 and a tip portion 62 connecting to the installing portion 61. The column tip 7 comprises an installing portion 71, an abutting portion 72 and a tip portion 73 connecting to the abutting portion 72, wherein the length D2 of the tip portion 73 is less than the depth D1 of the collection tube 8 (as shown in FIG. 3C). Accordingly, when the tip portion 73 loaded with the nucleic acids enters the collection tube 8, this design can prevent the sample with nucleic acids from being splashed out of the collection tube 8 caused by the excessive force due to the ejected sample from the tip portion 73, so as to improve the yield of nucleic acid extraction. In this embodiment, the installing portion 61 and the tip portion 62 can be integrally formed as one piece, and the installing portion 71, the abutting portion 72 and the tip portion 73 can be integrally formed as one piece.

Alternatively, the installing portion 61 and the tip portion 62 can be detachable parts, and the installing portion 71, the abutting portion 72 and the tip portion 73 can be detachable parts. This disclosure is not limited. In particular, the sample tip 6 and the column tip 7 may have similar structure. The difference between the sample tip 6 and the column tip 7 is that the column tip 7 comprises a membrane 74, while the sample tip 6 does not comprise the membrane 74. That is, the sample tip 6 also comprises an installing portion, an abutting portion and a tip portion, so that the sample tip 6 and the column tip 7 can be manufactured by a single mold, and the membrane 74 is configured to form the column tip 7 (the membrane 74 is not configured to form the sample tip 6).

Referring to FIGS. 3B to 5B, the bottom portion of the syringe 5 further comprises a joint 51, wherein the syringe 5 is connected to the installing portions 61 or 71 through the joint 51. In details, the joint 51 matches the structure of the installing portion of the sample tip 6 or the installing portion 71 of the column tip 7 so as to tightly connect the syringe 5 with the installing portion 61 or 71. In particular, the syringe 5 and the joint 51 can be integrally formed as one piece.

Figure 7A:
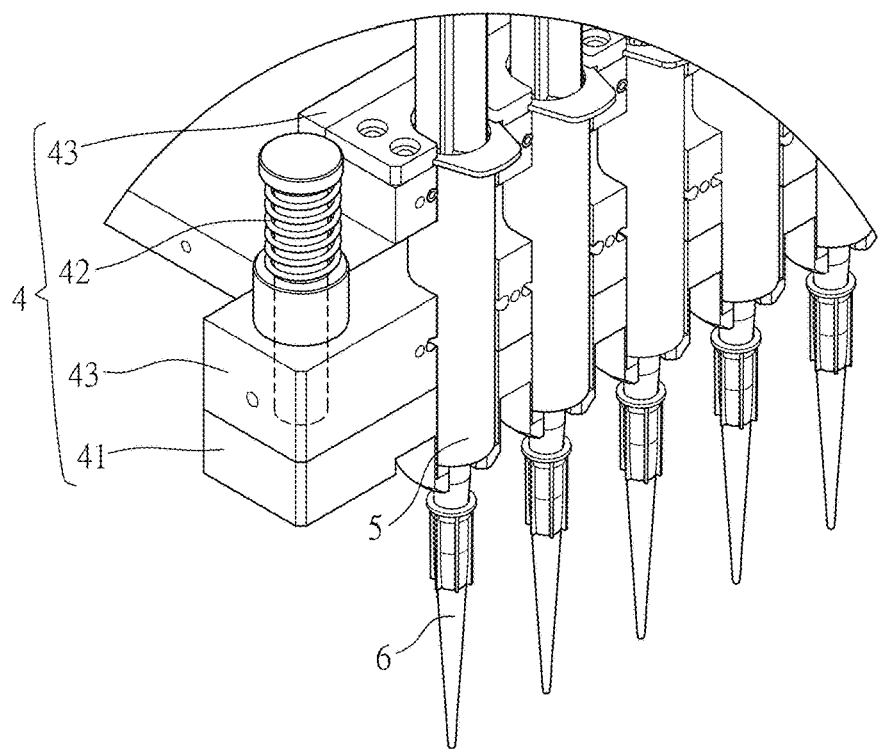
FIG. 7A is a partial enlarged view of the automated nucleic acid extraction device of FIG. 1.
Figure 7B:
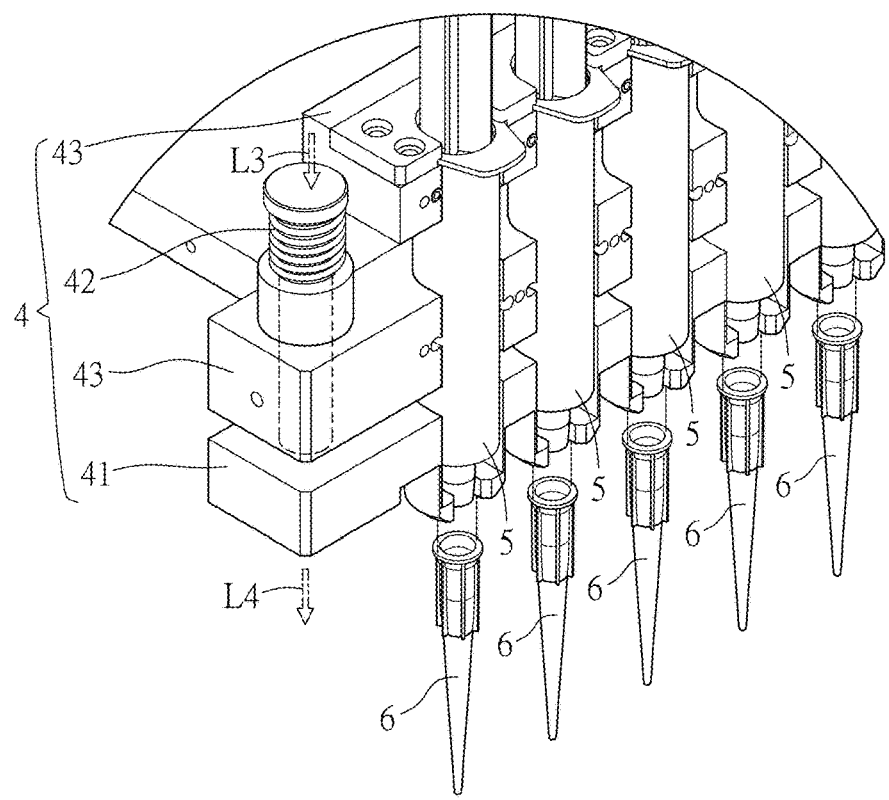
FIG. 7B is a schematic diagram showing an operation of the automated nucleic acid extraction device of FIG. 7A.

FIG. 7A is a partial enlarged view of the automated nucleic acid extraction device of FIG. 1. Referring to FIG. 1 and FIGS. 7A to 7B, the moving frame 4 comprises an ejector plate 41, and two spring mechanisms 42 are configured at two sides of the moving frame 4, respectively. The spring mechanisms 42 can carry the ejector plate 41 to move so as to control the detachment of the installing portions 61 or 71 from the bottom portions of the syringes 5. In details, as shown in FIG. 7B, the spring mechanisms 42 can move in the direction L3 so as to carry the ejector plate 41 to move in the direction L4, thereby separating the sample tips 6 or the column tips 7 from the syringes 5.

Figure 7C:
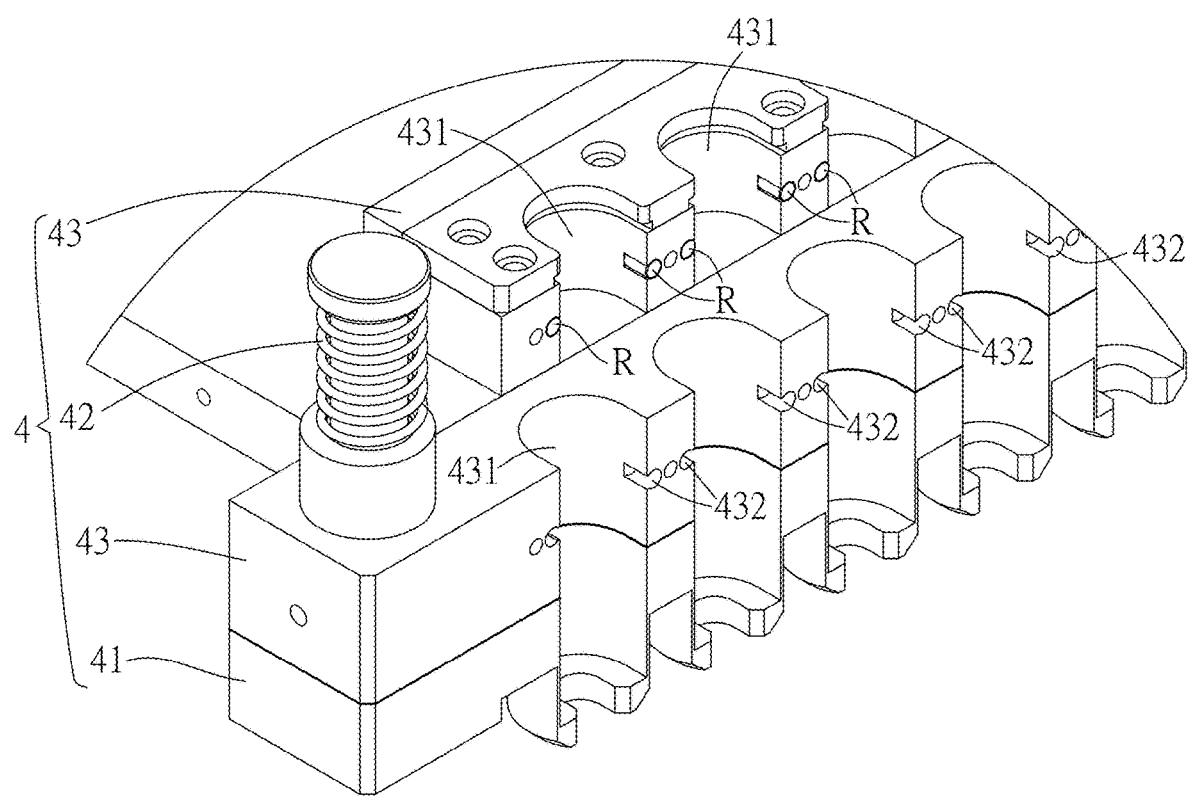
FIG. 7C is another schematic diagram of the automated nucleic acid extraction device of FIG. 7A.

Referring to FIG. 7C in view of FIG. 7A, the moving frame 4 further comprises at least one syringe fixing member 43 for fixing the syringe 5 on the moving frame 4. The syringe fixing member 43 can further comprise a syringe engage hole 431 and at least one concave hole 432, and the concave hole 432 can be configured with an elastic member R. As shown in FIG. 7A, each syringe 5 is fixed in the syringe engage holes 431 of two syringe fixing members 43, and is firmly fixed in the syringe engage holes 431 by the elastic members R configured in the concave holes 432. In particular, the numbers of the syringe fixing members 43, the concave holes 432 and the elastic members R can be adjusted according to the needs of user, and any configuration that can firmly fix the syringe 5 in the syringe engage holes 431 is acceptable. This disclosure is not limited.

Figure 5A:
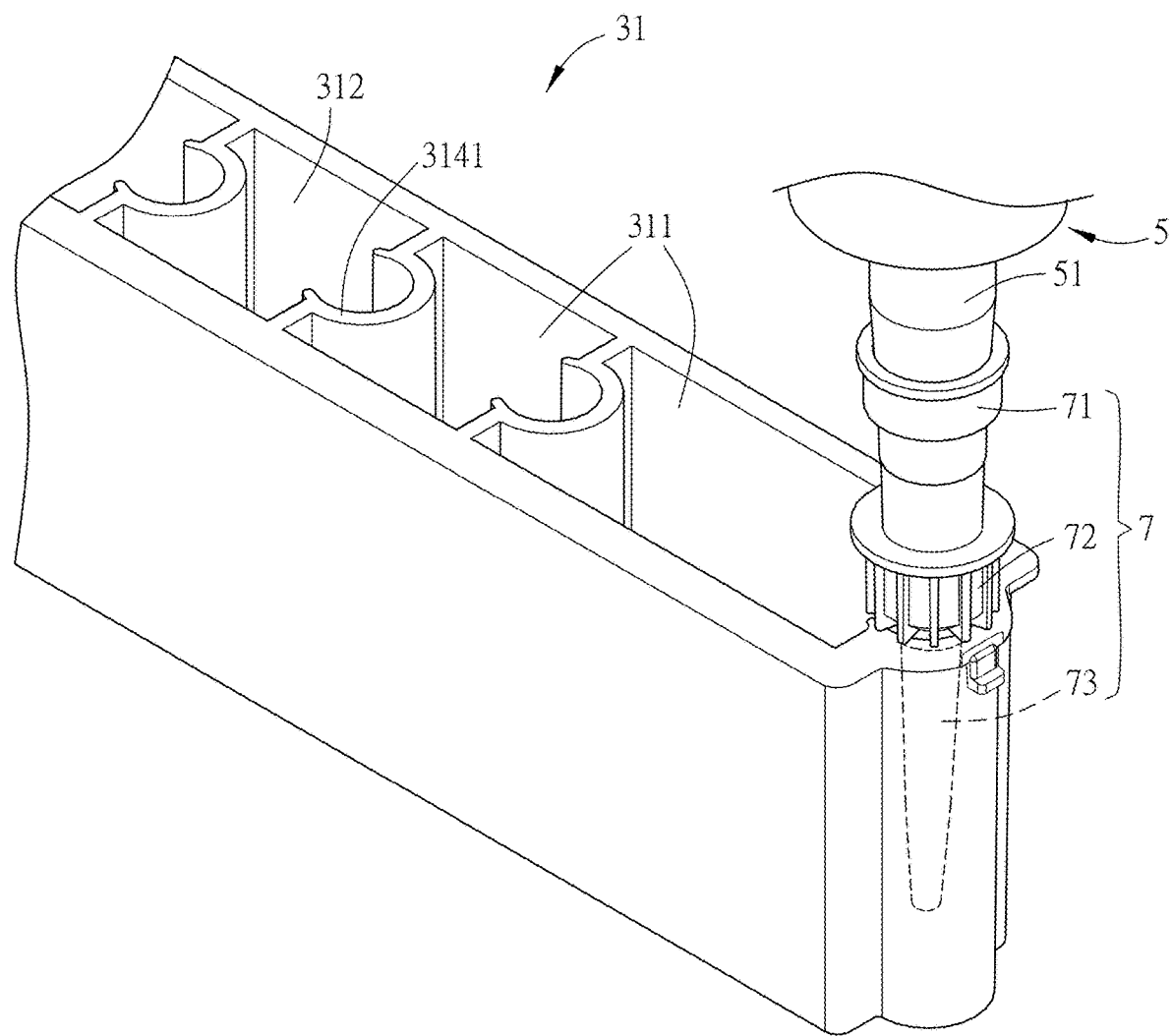
FIG. 5A is a partial view of the automated nucleic acid extraction device according to an embodiment of this disclosure.
Figure 5B:
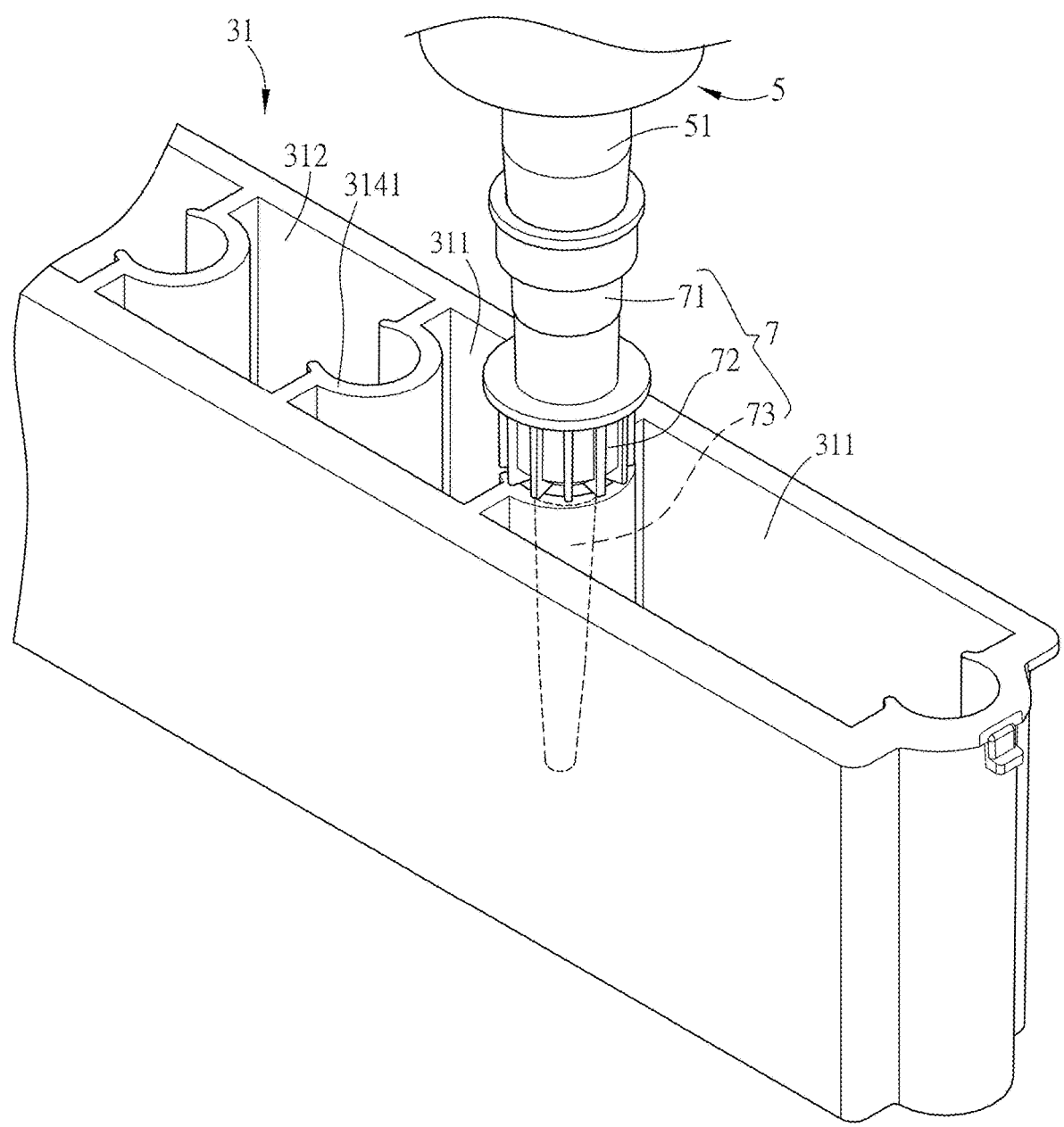
FIG. 5B is a partial view of the automated nucleic acid extraction device according to an embodiment of this disclosure.

Please refer to FIGS. 1, 5A, 5B and 6A, wherein FIGS. 5A and 5B are partial views of the automated nucleic acid extraction device according to an embodiment of this disclosure, and FIG. 6A is a top view of a cassette of the automated nucleic acid extraction device according to an embodiment of this disclosure. As shown in FIGS. 5A, 5B and 6A, the load-bearing abutment 314 is provided with an arcuate wall 3141, and the arc angle θ of the arcuate wall 3141 is greater than or equal to 90 degrees. Preferably, the arc angle θ is 90 degrees; preferably, the arc angle θ is 120 degrees; preferably, the arc angle θ is 180 degrees; or preferably, the arc angle θ is 270 degrees. Any configuration that can be provided for the column tip 7 to contact with and stand is acceptable. In particular, as shown in FIG. 6A, the vertical wall 31b has the arcuate wall 3141. Since the vertical wall 31b is connected to the parallel wall 31a, the two ends of the arcuate wall 3141 are not directly connected to the parallel wall 31a.

Figure 5C:
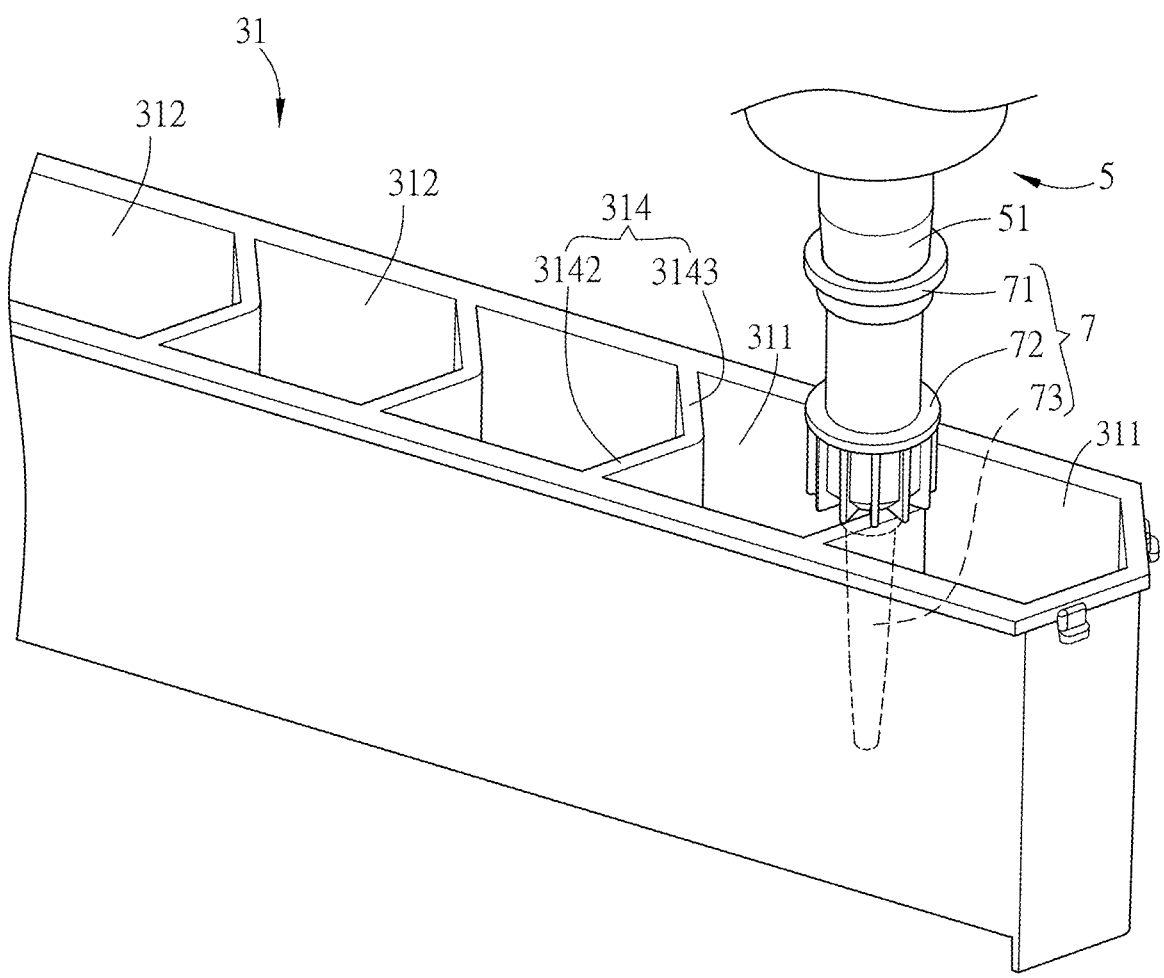
FIG. 5C is a partial view of the automated nucleic acid extraction device according to an embodiment of this disclosure.
Figure 6D:
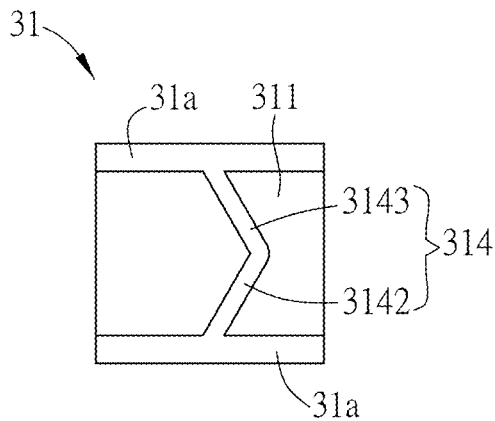
FIGS. 6D to 6H are schematic diagrams showing different aspects of the load-bearing abutments of the cassette of the automated nucleic acid extraction device of this disclosure.
Figure 6E:
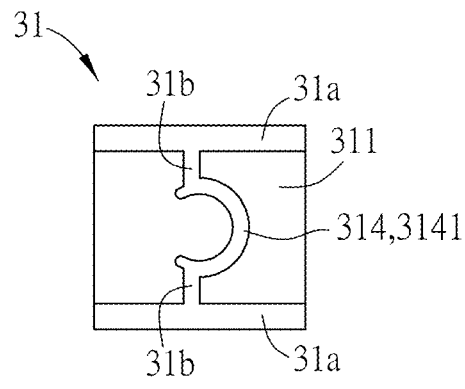
Figure 6F:
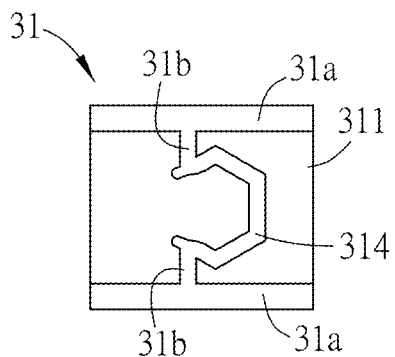
Figure 6G:
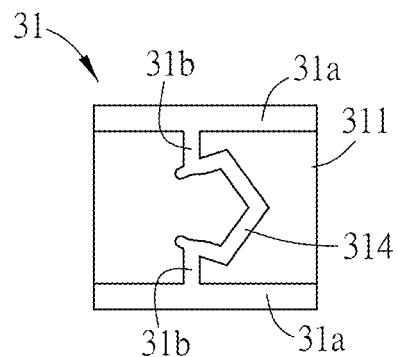
Figure 6H:
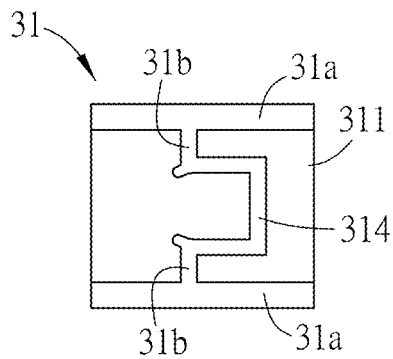

Please refer to FIGS. 1, 5C and 6C, wherein FIG. 5C is a partial view of the automated nucleic acid extraction device according to an embodiment of this disclosure, and FIG. 6C is a top view of a cassette of the automated nucleic acid extraction device according to another embodiment of this disclosure. As shown in FIGS. 5C and 6C, the load-bearing abutment 314 has a polygonal wall, which comprises at least two supporting walls. In this embodiment, the polygonal wall of the load-bearing abutment 314 comprises a first supporting wall 3142 and a second supporting wall 3143 for example, and an included angle e between the first supporting wall 3142 and the second supporting wall 3143 is less than 180 degrees. Preferably, the included angle e is 150 degrees; preferably, the included angle e is 120 degrees; preferably, the included angle e is 90 degrees; or preferably, the included angle e is 45 degrees. Any configuration that can be provided for the column tip 7 to contact with and stand is acceptable. In particular, different aspects of the load-bearing abutment of the cassette of the automated nucleic acid extraction device of this disclosure will be described with reference to FIGS. 6D to 6H. The load-bearing abutment 314 comprises, for example but not limited to, an arcuate wall 3141 (see FIG. 6E) or a polygonal wall (see FIG. 6D and FIGS. 6F to 6H). The structure of polygonal wall comprises, for example but not limited to, two supporting walls, three supporting walls, four supporting walls, five supporting walls, six supporting walls, or more than six supporting walls. Any adjacent two supporting walls have an included angle, and the number of the supporting walls and the size of the included angle are not limited. Any configuration that can be provided for the column tip 7 to contact with and stand is acceptable. In particular, as shown in FIG. 6D, the two ends of the polygonal wall of the load-bearing abutment 314 can be directly connected with the parallel wall 31a. However, as shown in FIGS. 6F to 6H, the vertical wall 31b is connected with the parallel wall 31a, but the two ends of the polygonal wall of the load-bearing abutment 314 of the vertical wall 31b is not directly connected with the parallel wall 31a. This disclosure is not limited.

Through the design of the load-bearing abutment 314, in the process of ejecting liquid (e.g. reactant, wash buffer, etc.), the abutting portion 72 of the column tip 7 abuts against the arcuate wall 3141 of the load-bearing abutment 314 or between the first supporting wall 3142 and the second supporting wall 3143. Thus, when the syringe 5 ejects liquid, the column tip 7 will not fall off and separate from the syringe 5 due to excessive pressure. Even if the column tip 7 is loosened when the syringe 5 rises after ejecting liquid, the configuration of the load-bearing abutment 314 can make the abutting portion 72 of the column tip 7 abut and stand on the load-bearing abutment 314 without being completely separated from the syringe 5. Afterwards, the following step can move the syringe 5 up and down in the direction L2, which is perpendicular to the linear direction L1, so as to tightly fit the syringe 5 and the column tip 7 again, thereby benefiting the subsequent extraction steps.

Please refer to FIGS. 1, 6A and 6B, wherein FIG. 6B is a top view of a cassette of the automated nucleic acid extraction device according to another embodiment of this disclosure. In the cassette as shown in FIG. 6B, the vertical wall 31b located between the wash buffer well 312 and the elution buffer well 313 has a complete hollow cylindrical structure so as to form a filter accommodating space 315 for accommodating a filter. In details, when the biological sample is a tissue or any sample containing impurities, the filter can be used to filter the dissolved lysate to secure the tissue fragments or impurities on the outside of the filter, and then the clear lysate (without tissue fragments or impurities) can be sucked into the sample tip 6. This configuration can avoid the tip portion 62 of the sample tip 6 from being blocked by the tissue fragments or impurities. Based on this design, the tissue sample can be directly loaded to the machine without the step of centrifugal to obtain clear lysate in advance. Therefore, the step of lysing the tissue sample can be completed on the automated nucleic acid extraction device of the present disclosure, so that the effect of automatic nucleic acid purification of the tissue sample can also be achieved. In particular, when the ribonucleic acid (RNA) in the sample is to be extracted, the filter accommodating space 315 can further accommodate the enzymes required in the extraction process, such as deoxyribonuclease (DNase), to remove the deoxyribonucleic acid (DNA) in the sample during the extraction process. Besides, the DNase can also be washed and removed in the subsequent washing steps, so after the extraction is completed, the RNA (without DNA) can be obtained.

Referring to FIGS. 1 and 2, in this experimental example, the moving frame 4 and the syringe 5 move in the linear direction L1 (that is, with relative to the desktop, the syringe moves but the cassette does not move), so the depth of the machine is only the sum of the length D3 of the base body B and the thickness D4 of the moving frame 4 (D3+D4). However, the conventional art is to move the base body B linearly. In order to enable the syringes to suck the solutions in each accommodating space, the depth of the machine must be at least twice the length D3 of the base body B plus the thickness D4 of the moving frame 4 (D3×2+D4). For example, if the length D3 of the base body B of the automated nucleic acid extraction device of this experimental example is, for example but not limited to, 30 cm, and the thickness D4 of the moving frame 4 is, for example but not limited to, 20 cm, the depth of the machine will be, for example but not limited to, about 50 cm. Therefore, the operation space of the user can be saved.

Figure 9:
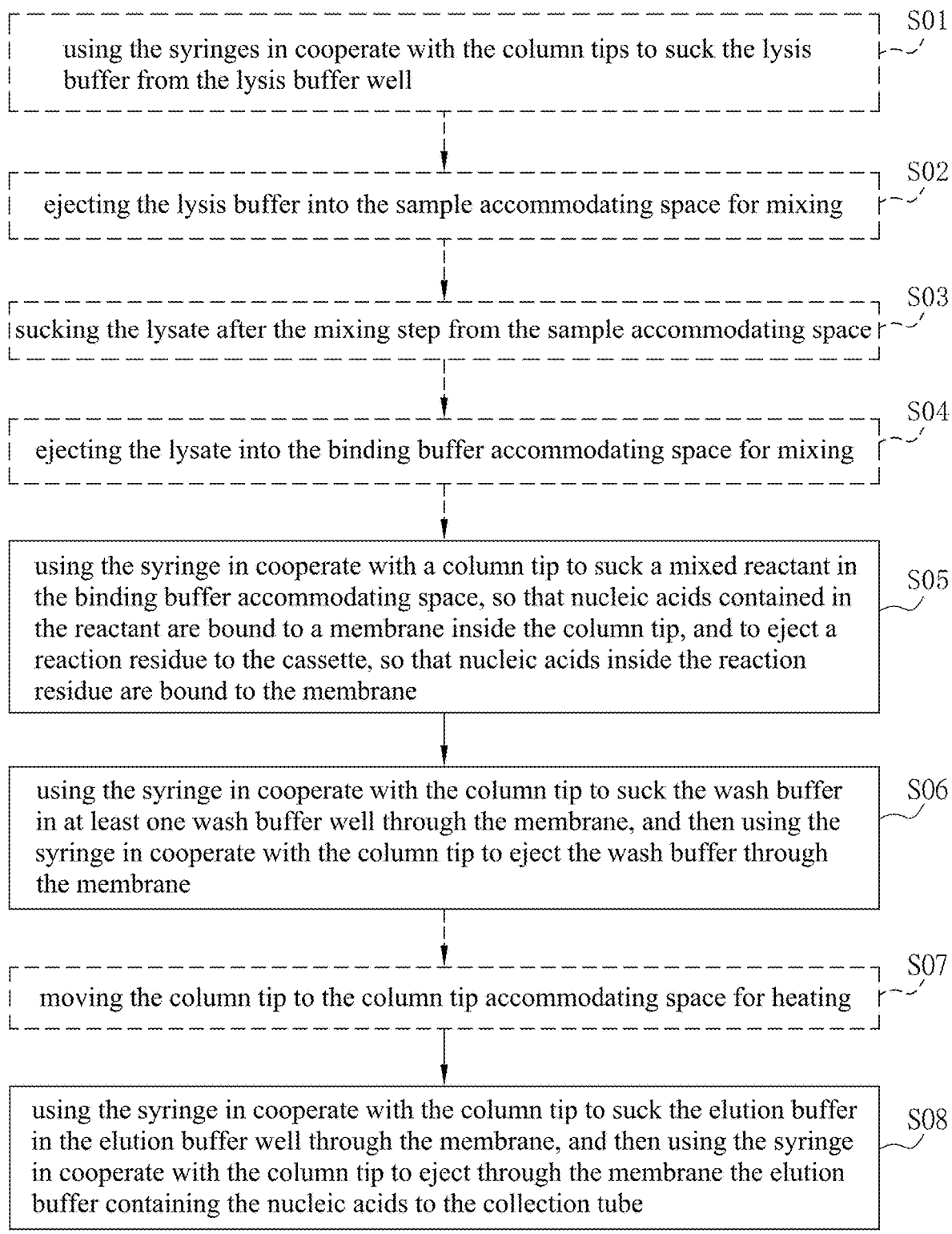
FIG. 9 is a flow chart showing an automated nucleic acid extraction method according to an embodiment of this disclosure.

An automated nucleic acid extraction method according to an embodiment of this disclosure will be described with reference to FIG. 9 in view of FIGS. 1 to 3C, wherein the automated nucleic acid extraction method is applied to the above-mentioned automated nucleic acid extraction device. The bottom portion of the automated nucleic acid extraction device is configured with a transmission belt, which can carry the moving frame 4 to move in the linear direction L1. In this embodiment, the automated nucleic acid extraction method comprises the following steps of: a step S05 to use the syringe 5 in cooperate with the column tip 7 to suck a mixed reactant in the binding buffer accommodating space, so that nucleic acids contained in the reactant are bound to a membrane 74 inside the column tip 7, and to eject a reaction residue to the cassette 31, so that nucleic acids inside the reaction residue are bound to the membrane 74; a step S06 to use the syringe 5 in cooperate with the column tip 7 to suck the wash buffer in at least one wash buffer well through the membrane 74, and then to use the syringe 5 in cooperate with the column tip 7 to eject the wash buffer through the membrane 74; and a step S08 to use the syringe 5 in cooperate with the column tip 7 to suck the elution buffer in the elution buffer well through the membrane 74, and then to use the syringe 5 in cooperate with the column tip 7 to eject through the membrane 74 the elution buffer containing the nucleic acids to the collection tube 8. Herein, between the steps S06 and S08, a step S07 can be provided to move the column tip 7 to the column tip accommodating space 22 for heating so as to reduce the amount of wash buffer remaining on the membrane 74 as much as possible. The above steps S05 to S08 are performed by the automated nucleic acid extraction device. The dashed blocks shown in FIG. 9 (steps S01 to S04) can be performed manually by the user outside the automated nucleic acid extraction device, or all by the automated nucleic acid extraction device. For example, the user can first dissolve the sample, centrifuge the solution, mix the supernatant with the binding buffer, and then add the mixture into the binding buffer accommodating space, and then the automated nucleic acid extraction device can perform the subsequent steps. Alternatively, the user can first dissolve the sample, centrifuge the solution, and add the supernatant into the binding buffer accommodating space for mixing with the binding buffer, and then the automated nucleic acid extraction device can perform the subsequent steps. Alternatively, the user can first dissolve the sample, centrifuge the solution, and add the lysate into the lysis buffer well, and then the automated nucleic acid extraction device can perform the subsequent steps. This disclosure is not limited.

This embodiment illustrates the case of using the automated nucleic acid extraction device to perform the steps S01 to S08. In the steps S01 to S08, the automated nucleic acid extraction device and the moving frame 4 (carrying the syringes 5) move to a specific position in the linear direction L1 for performing the above-mentioned steps. The details will be described hereinafter. Before the step S01, the syringes 5 disposed on the moving frame 4 are moved in the linear direction L1 to the sample tip accommodating space 21 of the column accommodating area 2, so that the syringes 5 can be connected to the sample tips 6 arranged in the sample tip accommodating space 21, and then the sample tips 6 can be retrieved from the sample tip accommodating space 21. Next, the sample tips 6 connected to the syringes 5 are moved in the linear direction L1 to the cassette 31 in the cassette accommodating area 3. After that, the step S01 is performed to suck the lysis buffer from the lysis buffer well 311 of the cassette, and then to move to the sample accommodating area 1. Next, the step S02 is performed to eject the lysis buffer into the sample accommodating space 11 of the sample accommodating area 1 for mixing. After that, the step S03 is performed to suck the lysate after the mixing step from the sample accommodating space 11, and to move to the binding buffer accommodating space 12 of the sample accommodating area 1. Then, the step S04 is performed to eject the lysate into the binding buffer accommodating space 12 for mixing with the binding buffer so as to performing the binding reaction. Afterwards, before performing the step S05, the syringes 5 and the sample tips 6 are moved to the sample tip accommodating space 21, the spring mechanisms 42 act to drive the ejector plate 41 to detach the sample tips 6 from the syringes 5 and to load the sample tips 6 into the sample tip accommodating space 21, the syringes 5 are moved in the linear direction L1 to the column tip accommodating space 22 of the column accommodating area 2, and the syringes 5 can be connected to the column tips 7 arranged in the column tip accommodating space 22 so as to retrieve the column tips 7 configured with the membranes 74 therein from the column accommodating area 2. Then, the column tips 7, which are connected to the syringes 5, are moved to the binding buffer accommodating space 12. The step S05 is then performed to use the syringes 5 in cooperate with the column tips 7 to suck the formed reactant, and to make the reactant pass through the membranes 74, so that the nucleic acids contained in the reactant are bound to the membranes 74 inside the column tips 7. Afterwards, the syringes 5 are moved to the cassette 31 in the linear direction L1. Then, the reactant flows in the gravity direction and passes through the membrane 74, so that the nucleic acids contained in the reactant are bound to the membranes 74. Meanwhile, the reactant residue will flow in the gravity direction and be ejected to the cassette 31. Herein, the reactant residue can pass through the membranes twice so as to ensure the nucleic acids contained in the reactant residue to be bound to the membranes 74. The step S06 is then performed. The column tips 7 containing the nucleic acids are moved in the linear direction L1 along with the syringes 5 and the moving frame 4 to the wash buffer wells 312, which contain the wash buffer. The wash step is performed by sucking and ejecting the wash buffer, so that the wash buffer can flow through the membranes 74 twice, thereby washing and cleaning the reactant residue remained on the membranes 74. After the wash step, the column tips 7 containing the nucleic acids are moved in the linear direction L1 along with the syringes 5 and the moving frame 4 to the column tip accommodating space 22, and the column tips 7 are stayed in the column tip accommodating space 22 and heated by the heaters H to evaporate the liquid (e.g. the wash buffer) remained on the membranes 74 of the column tips 7 so as to sufficiently dry the membranes 74 (i.e., the step S07). Finally, the column tips 7 containing the nucleic acids are moved in the linear direction L1 along with the syringes 5 and the moving frame 4 to the elution buffer wells 313 containing the elution buffer to perform the step S08. The elution step is performed by sucking and ejecting the elution buffer, thereby obtaining the eluate (the elution buffer containing the nucleic acids). Then, the column tips 7 can retrieve the obtained eluate, move to the collection tubes 8 in the linear direction L1, and eject the eluate to the collection tubes 8. In particular, the heating period of the heaters H can be, for example but not limited to, 30 seconds, 1 minute, 3 minute, or 5 minute, which is enough to evaporate and dry the remained liquid on the membranes 74 of the column tips 7, and this disclosure is not limited.

In this embodiment, in the step of ejecting the reactant residue to the cassette 31 (step S05) and the step of using the syringe 5 in cooperate with the column tip 7 to eject the wash buffer through the membrane 74, the abutting portion 72 of the column tip 7 abuts against the load-bearing abutment 314 of the cassette 31, and then the reactant residue or the wash buffer is ejected. Due to the design of the load-bearing abutment 314, the column tip 7 can abut against the load-bearing abutment 314 when the syringe 5 ejects liquid. Thus, when the syringe 5 ejects liquid, the column tip 7 will not fall off and separate from the syringe 5 due to excessive pressure. Even if the column tip 7 is loosened when the syringe 5 rises after ejecting liquid, the configuration of the load-bearing abutment 314 can make the abutting portion 72 of the column tip 7 abut and stand on the load-bearing abutment 314 without being completely separated from the syringe 5. Thus, the syringe 5 and the column tip 7 can be tightly fitted again by the following steps.

In this embodiment, after the steps of abutting the abutting portion 72 of the column tip 7 against the load-bearing abutment 314 of the cassette 31, and ejecting the reactant residue or wash buffer (the steps S05 and S06), the automated nucleic acid extraction method further comprises a step of: abutting the abutting portion 72 of the column tip 7 against the load-bearing abutment 314 of the cassette 31 and moving the syringe 5 in a direction L2 perpendicular to the linear direction L1 up and down for a distance less than or equal to 5 mm. According to this step, the column tip 7 can be tightly connected to the syringe 5 so as to prevent the column tip 7 from loosening and falling. Preferably, the syringe 5 can move up and down by 5 mm in the direction L2; preferably, the syringe 5 can move up and down by 4.5 mm in the direction L2; and preferably, the syringe 5 can move up and down by 3 mm in the direction L2, thereby tightly connecting the column tip 7 to the syringe 5 again.

In this embodiment, the number of the wash buffer wells 312 can be adjusted based on the requirement of the user, and this disclosure is not limited. In details, if the number of the wash buffer wells 312 is more than one, before moving the column tip 7 to the column tip accommodating space 22 and heating, the following step of using the syringe 5 in cooperate with the column tip 7 to suck the wash buffer in at least one wash buffer well through the membrane 74 and using the syringe 5 in cooperate with the column tip 7 to eject the wash buffer through the membrane 74 can be repeated for at least once. That is, the wash step of moving the column tip 7 containing the nucleic acids in the linear direction L1 along with the syringes 5 and the moving frame 4 to the wash buffer wells 312 containing the wash buffer and repeating the suction and ejection of the wash buffer can be performed in different wash buffer wells 312. The repeated number of the wash step can be determined based on the number of the wash buffer wells 312.

In this embodiment, between the step of ejecting the lysis buffer into the sample accommodating space 11 for mixing (step S02) and the step of sucking the lysate after the mixing step from the sample accommodating space 11 (step S03), the method further comprises a step of moving to the filter accommodating space 315 for assembling the sample tip 6 cooperated with the syringe 5 with the filter in the filter accommodating space 315. In addition, after the step of sucking the lysate after the mixing step from the sample accommodating space 11 (step S03), the method further comprises a step of moving the sample tip 6 and the filter to the lysis buffer wells 311 and reciprocating in the linear direction in the lysis buffer wells 311. In details, when the biological sample is tissue or other samples with impurities, the filter is configured to filter the dissolved lysate to block the tissue fragments or impurities at the outside of the filter, and then the step S03 is performed to suck the clear lysate (without tissue fragments or impurities) into the syringe 5. Then, the sample tip 6 and the filter are moved to the lysis buffer well 311 and reciprocated in a linear direction in the lysis buffer well 311 to wash away the impurities stuck on the outside of the filter, and then the lysate in the syringe 5 is ejected to the binding buffer accommodating space 12 for performing the binding reaction. This configuration can prevent tissue fragments or impurities from affecting the effect of the binding reaction and thus the extraction efficiency. That is, when the biological sample is tissue or other samples with impurities, the aforementioned steps can be added.

In this embodiment, the numbers of the sample accommodating space 11, the binding buffer accommodating space 12, the sample tip accommodating space 21, the column tip accommodating space 22, the lysis buffer well 311, the wash buffer well 312, the elution buffer well 313, the load-bearing abutment 314, the syringe 5, the sample tip 6, the column tip 7, the collection tube 8, and the joint 51 can be adjusted based on the actual requirement of the user, and this disclosure is not limited. In particular, the cassette 31, the sample accommodating space 11, the binding buffer accommodating space 12, the sample tip accommodating space 21, the column tip accommodating space 22, the syringe 5 and the collection tube 8 can be arranged in the linear direction L1, and the order of their arrangement is not limited.

In summary, each of the lysis buffer wells 311, the wash buffer wells 312 and the adjacent elution buffer wells 313 of the automated nucleic acid extraction device is configured with a load-bearing abutment 314, so that it can avoid the reactant from being splashed from the lysis buffer wells 311, the wash buffer wells 312 or the adjacent elution buffer wells 313, and can prevent the column tip 7 from loosening and falling. In addition, since the cassette 31 and the accommodating space are arranged in a linear direction L1, and the moving frame 4 and the syringe 5 can reciprocate in the linear direction L1, the effect of automated nucleic acid extraction in the linear direction L1 can be achieved, thereby avoiding sample contamination and improving extraction efficiency. Accordingly, the automated nucleic acid extraction device of the present disclosure can indeed rapidly and conveniently extract nucleic acids (e.g. cfDNA and ctDNA) with a higher yield and a higher concentration from the specimen.

Although the disclosure has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the disclosure.

What is claimed is:

1. An automated nucleic acid extraction device, comprising:
    a base body comprising a sample accommodating area, a column accommodating area comprising a sample tip accommodating space and a column tip accommodating space, a cassette accommodating area and a collection tube, wherein the sample accommodating area, the column accommodating area, the cassette accommodating area and the collection tube are arranged in a linear direction;
    a sample tip and a column tip each comprising an abutting portion, wherein the sample tip and the column tip are movably disposed in the sample tip accommodating space and the column tip accommodating space, respectively;
    a cassette arranged in the cassette accommodating area, wherein the cassette includes two parallel outer walls and at least four vertical walls, the parallel outer walls are arranged on the base body vertically, each of the vertical walls is arranged between the parallel outer walls and two sides of each of the vertical walls are connected to the parallel outer walls, respectively, the vertical walls divide a space between the parallel outer walls to jointly form a lysis buffer well, at least one wash buffer well and an elution buffer well, each of the vertical walls forming the lysis buffer well, the at least one wash buffer well and the elution buffer well includes a load-bearing abutment, the lysis buffer well, the at least one wash buffer well and the elution buffer well are arranged in the linear direction, and the load-bearing abutment is provided with an arcuate wall having an arc angle greater than or equal to 90 degrees or a polygonal wall comprising at least two supporting walls, wherein an included angle between the supporting walls is less than 180 degrees;
    a driving unit arranged on the base body;
    a moving frame arranged on the base body vertically and driven by the driving unit to reciprocate in the linear direction; and
    a syringe arranged on the moving frame and being moved along with the moving frame, wherein the syringe is detachably connectable to the sample tip or the column tip,
    wherein the driving unit drives the moving frame and the moving frame carries the syringe, causing the syringe to move to the sample accommodating area, the column accommodating area, the cassette accommodating area and the collection tube,
    wherein the abutting portion of the sample tip or the column tip is configured to be abutted against the load-bearing abutment of each of the vertical walls when the syringe is connected to the sample tip or the column tip and the driving unit has moved the syringe with the moving frame to the cassette.

2. The automated nucleic acid extraction device of claim 1, wherein the sample accommodating area comprises a sample accommodating space and a binding buffer accommodating space.

3. The automated nucleic acid extraction device of claim 1, wherein the vertical wall between the wash buffer well and the elution buffer well has a complete hollow cylindrical structure so as to form a filter accommodating space.

4. The automated nucleic acid extraction device of claim 1, wherein a bottom portion of the elution buffer well is provided with a recess portion, and the cassette further comprises an elastic fastener.

* * * * *